US012108964B2

(12) United States Patent
Aljuri et al.

(10) Patent No.: US 12,108,964 B2
(45) Date of Patent: *Oct. 8, 2024

(54) MINIMALLY INVASIVE TISSUE TREATMENT DEVICE

(71) Applicant: AquaBeam, LLC, Hillsborough, CA (US)

(72) Inventors: Nikolai Aljuri, Hillsborough, CA (US); Rodney C. Perkins, Woodside, CA (US)

(73) Assignee: AquaBeam, LLC, Hillsborough, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/048,296

(22) Filed: Oct. 20, 2022

(65) Prior Publication Data
US 2023/0063051 A1 Mar. 2, 2023

Related U.S. Application Data

(60) Division of application No. 16/392,984, filed on Apr. 24, 2019, now Pat. No. 11,478,269, which is a (Continued)

(51) Int. Cl.
*A61B 18/14* (2006.01)
*A61B 17/3203* (2006.01)
(Continued)

(52) U.S. Cl.
CPC .... *A61B 17/3203* (2013.01); *A61B 17/32037* (2013.01); *A61B 18/04* (2013.01);
(Continued)

(58) Field of Classification Search
CPC ........... A61B 2017/00234; A61B 2017/00238; A61B 2017/00274; A61B 2017/22079;
(Continued)

(56) References Cited

U.S. PATENT DOCUMENTS 3,763,860 A 10/1973 Clarke
3,818,913 A 6/1974 Wallach
(Continued)

FOREIGN PATENT DOCUMENTS

CA 2330436 A1 11/2009
CN 1137230 A 12/1996
(Continued)

OTHER PUBLICATIONS

Balicki, et al., "Single fiber optical coherence tomography microsurgical instruments for computer and robot-assisted retinal surgery". Medical Image Computing and Computer-Assisted Intervention. G.-Z. Yang et al. (Eds.): MICCAI 2009, Part I, LNCS 5761, pp. 108-115, 2009.
(Continued)

*Primary Examiner* — Ahmed M Farah
(74) *Attorney, Agent, or Firm* — FisherBroyles, LLP; John K. Shimmick

(57) ABSTRACT

Prostate treatment using fluid stream to resect prostate tissue, thereby relieving symptoms of conditions such as BPH, prostatitis, and prostatic carcinoma. A device having a fluid delivery element is positioned within a lumen of the urethra within the prostate. A fluid stream is directed outwardly from the fluid delivery element toward a wall of the urethral lumen. The fluid delivery element is moved to scan the fluid stream over the wall to remove a volume of tissue surrounding the lumen. The fluid may be combined with therapeutically active substances or with substances that increase resection efficiency. Fluid force may be adjusted to provide selective tissue resection such that soft tissue is removed while harder tissue is left undamaged. In order to gain a working space within the urethra, another fluid may be introduced to insufflate the urethra in the region of treatment.

13 Claims, 21 Drawing Sheets

Related U.S. Application Data continuation of application No. 14/956,199, filed on Dec. 1, 2015, now Pat. No. 10,321,931, which is a continuation of application No. 13/790,218, filed on Mar. 8, 2013, now Pat. No. 9,232,960, which is a division of application No. 12/700,568, filed on Feb. 4, 2010, now Pat. No. 9,232,959, which is a continuation-in-part of application No. 12/399,585, filed on Mar. 6, 2009, now Pat. No. 8,814,921, and a continuation-in-part of application No. 11/968,445, filed on Jan. 2, 2008, now Pat. No. 7,882,841.

(60) Provisional application No. 61/097,497, filed on Sep. 16, 2008, provisional application No. 61/034,412, filed on Mar. 6, 2008, provisional application No. 60/883,097, filed on Jan. 2, 2007.

(51) Int. Cl.
| | |
|---|---|
| *A61B 18/04* | (2006.01) |
| *A61B 18/18* | (2006.01) |
| *A61B 18/20* | (2006.01) |
| *A61B 18/24* | (2006.01) |
| *A61F 9/007* | (2006.01) |
| *A61B 17/00* | (2006.01) |
| *A61B 17/22* | (2006.01) |
| *A61B 18/00* | (2006.01) |

(52) U.S. Cl.
CPC .......... *A61B 18/14* (2013.01); *A61B 18/1485* (2013.01); *A61B 18/18* (2013.01); *A61B 18/201* (2013.01); *A61B 18/24* (2013.01); *A61F 9/007* (2013.01); *A61F 9/00736* (2013.01); *A61B 2017/00274* (2013.01); *A61B 2017/22079* (2013.01); *A61B 2018/00196* (2013.01); *A61B 2018/00285* (2013.01); *A61B 2018/00547* (2013.01); *A61B 2018/00577* (2013.01); *A61B 2018/00583* (2013.01); *A61B 2018/00946* (2013.01); *A61B 2018/00952* (2013.01); *A61B 2018/046* (2013.01); *A61B 2018/1472* (2013.01); *A61B 2018/1497* (2013.01); *A61B 2018/1861* (2013.01); *A61B 2218/002* (2013.01); *A61B 2218/007* (2013.01)

(58) Field of Classification Search
CPC ........ A61B 17/3203; A61B 2017/3203; A61B 2017/32035; A61B 17/32037; A61B 18/14; A61B 18/1452; A61B 18/1485; A61B 18/1861; A61B 18/24; A61B 18/245; A61B 18/26; A61B 2018/02; A61B 2018/00196; A61B 2018/00214; A61B 2018/0022; A61B 2018/00244; A61B 2018/00315; A61B 2018/00327; A61B 2018/00333; A61B 2018/00339; A61B 2018/00345; A61B 2018/00351; A61B 2018/00404; A61B 2018/00452; A61B 2018/00482; A61B 2018/00488; A61B 2018/00505; A61B 2018/00511; A61B 2018/00529; A61B 2018/00541; A61B 2018/00547; A61B 2018/00559; A61B 2018/00565; A61B 2018/00571; A61B 2018/00577; A61B 2018/00601; A61B 2018/00946; A61B 2018/00952
USPC ......... 606/2.5, 7, 13–15, 41, 45; 607/88, 89, 607/92, 101, 104, 105
See application file for complete search history.

(56) References Cited

U.S. PATENT DOCUMENTS

| | | |
|---|---|---|
| 3,821,510 A | 6/1974 | Muncheryan |
| 3,847,988 A | 11/1974 | Gold |
| 3,875,229 A | 4/1975 | Gold |
| 4,024,866 A | 5/1977 | Wallach |
| 4,040,413 A | 8/1977 | Ohshiro |
| 4,097,578 A | 6/1978 | Perronnet |
| 4,198,960 A | 4/1980 | Utsugi |
| 4,220,735 A | 9/1980 | Dieck |
| 4,239,776 A | 12/1980 | Bayles |
| 4,377,584 A | 3/1983 | Rasmusson |
| 4,386,080 A | 5/1983 | Crossley |
| 4,389,071 A | 6/1983 | Johnson, Jr. |
| 4,461,283 A | 7/1984 | Doi |
| 4,469,098 A | 9/1984 | Davi |
| 4,470,407 A | 9/1984 | Hussein |
| 4,474,251 A | 10/1984 | Johnson, Jr. |
| 4,532,935 A | 8/1985 | Wang |
| 4,560,373 A | 12/1985 | Sugino |
| 4,597,388 A | 7/1986 | Koziol |
| 4,636,505 A | 1/1987 | Tucker |
| 4,672,963 A | 6/1987 | Barken |
| 4,685,458 A | 8/1987 | Leckrone |
| 4,747,405 A | 5/1988 | Leckrone |
| 4,760,071 A | 7/1988 | Rasmusson |
| 4,776,349 A | 10/1988 | Nashef |
| 4,854,301 A | 8/1989 | Nakajima |
| 4,898,574 A | 2/1990 | Uchiyama |
| 4,905,673 A | 3/1990 | Pimiskern |
| 4,913,698 A | 4/1990 | Ito |
| 4,983,165 A | 1/1991 | Loiterman |
| 5,029,574 A | 7/1991 | Shimamura |
| 5,037,431 A | 8/1991 | Summers |
| 5,085,659 A | 2/1992 | Rydell |
| 5,116,615 A | 5/1992 | Gokcen |
| 5,135,482 A | 8/1992 | Neracher |
| 5,196,023 A | 3/1993 | Martin |
| 5,207,672 A | 5/1993 | Roth |
| 5,217,465 A | 6/1993 | Steppe |
| 5,224,939 A | 7/1993 | Holman |
| 5,242,438 A | 9/1993 | Saadatmanesh |
| 5,257,991 A | 11/1993 | Fletcher |
| 5,267,341 A | 11/1993 | Shearin |
| 5,269,785 A | 12/1993 | Bonutti |
| 5,308,323 A | 5/1994 | Sogawa |
| 5,318,589 A | 6/1994 | Lichtman |
| 5,320,617 A | 6/1994 | Leach |
| 5,322,503 A | 6/1994 | Desai |
| 5,322,504 A | 6/1994 | Doherty |
| 5,325,848 A | 7/1994 | Adams |
| 5,338,292 A | 8/1994 | Clement |
| 5,342,381 A | 8/1994 | Tidemand |
| 5,344,395 A | 9/1994 | Whalen |
| 5,353,783 A | 10/1994 | Nakao |
| 5,370,609 A | 12/1994 | Drasler |
| 5,372,124 A | 12/1994 | Takayama |
| 5,409,483 A | 4/1995 | Campbell |
| 5,411,016 A | 5/1995 | Kume |
| 5,425,735 A | 6/1995 | Rosen |
| 5,431,649 A | 7/1995 | Mulier |
| 5,441,485 A | 8/1995 | Peters |
| 5,449,356 A | 9/1995 | Walbrink |
| 5,450,843 A | 9/1995 | Moll |
| 5,454,782 A | 10/1995 | Perkins |
| 5,472,406 A | 12/1995 | De La Torre |
| 5,472,426 A | 12/1995 | Bonati |
| 5,496,267 A | 3/1996 | Drasler |
| 5,496,309 A | 3/1996 | Saadat |
| 5,501,667 A | 3/1996 | Verduin, Jr. |
| 5,505,729 A | 4/1996 | Rau |
| 5,514,669 A | 5/1996 | Selman |
| 5,520,684 A | 5/1996 | Imran |
| 5,527,330 A | 6/1996 | Tovey |
| 5,545,170 A | 8/1996 | Hart |
| 5,562,648 A | 10/1996 | Peterson |
| 5,562,678 A | 10/1996 | Booker |

(56) References Cited

U.S. PATENT DOCUMENTS

| | | |
|---|---|---|
| 5,562,703 A | 10/1996 | Desai |
| 5,572,999 A | 11/1996 | Funda |
| 5,573,535 A | 11/1996 | Viklund |
| 5,592,942 A | 1/1997 | Webler |
| 5,613,973 A | 3/1997 | Jackson |
| 5,620,414 A | 4/1997 | Campbell, Jr. |
| 5,630,794 A | 5/1997 | Lax |
| 5,645,083 A | 7/1997 | Essig |
| 5,649,923 A | 7/1997 | Gregory |
| 5,653,374 A | 8/1997 | Young |
| 5,658,311 A | 8/1997 | Baden |
| 5,662,590 A | 9/1997 | De La Torre |
| 5,666,954 A | 9/1997 | Chapelon |
| 5,672,153 A | 9/1997 | Lax |
| 5,672,171 A | 9/1997 | Andrus |
| 5,674,226 A | 10/1997 | Doherty |
| 5,695,500 A | 12/1997 | Taylor |
| 5,697,949 A | 12/1997 | Giurtino |
| 5,700,240 A | 12/1997 | Barwick, Jr. |
| 5,710,870 A | 1/1998 | Ohm |
| 5,716,325 A | 2/1998 | Bonutti |
| 5,733,256 A | 3/1998 | Costin |
| 5,733,277 A | 3/1998 | Pallarito |
| 5,753,641 A | 5/1998 | Gormley |
| 5,770,603 A | 6/1998 | Gibson |
| 5,772,657 A | 6/1998 | Hmelar |
| 5,773,791 A | 6/1998 | Kuykendal |
| 5,782,848 A | 7/1998 | Lennox |
| 5,785,521 A | 7/1998 | Rizoiu |
| 5,788,667 A | 8/1998 | Stoller |
| 5,792,165 A | 8/1998 | Klieman |
| 5,795,153 A | 8/1998 | Rechmann |
| 5,797,900 A | 8/1998 | Madhani |
| 5,810,770 A | 9/1998 | Chin |
| 5,817,649 A | 10/1998 | Labrie |
| 5,820,623 A | 10/1998 | Ng |
| 5,833,701 A | 11/1998 | Gordon |
| 5,836,909 A | 11/1998 | Cosmescu |
| 5,836,941 A | 11/1998 | Yoshihara |
| 5,861,002 A | 1/1999 | Desai |
| 5,871,462 A | 2/1999 | Yoder |
| 5,872,150 A | 2/1999 | Elbrecht |
| 5,893,869 A | 4/1999 | Barnhart |
| 5,897,491 A | 4/1999 | Kastenbauer |
| 5,902,499 A | 5/1999 | Richerzhagen |
| 5,907,893 A | 6/1999 | Zadno-Azizi |
| 5,924,175 A | 7/1999 | Lippitt |
| 5,989,230 A | 11/1999 | Frassica |
| 5,994,362 A | 11/1999 | Gormley |
| 6,022,860 A | 2/2000 | Engel |
| 6,033,371 A | 3/2000 | De La Torre |
| 6,056,738 A | 5/2000 | Marchitto |
| 6,066,130 A | 5/2000 | Gregory |
| 6,071,281 A | 6/2000 | Burnside |
| 6,071,284 A | 6/2000 | Fox |
| 6,093,157 A | 7/2000 | Chandrasekaran |
| 6,110,171 A | 8/2000 | Rydell |
| 6,117,128 A | 9/2000 | Gregory |
| 6,120,476 A | 9/2000 | Fung |
| 6,120,498 A | 9/2000 | Jani |
| 6,135,993 A | 10/2000 | Hussman |
| 6,142,991 A | 11/2000 | Schatzberger |
| 6,152,919 A | 11/2000 | Hakky |
| 6,156,030 A | 12/2000 | Neev |
| 6,174,318 B1 | 1/2001 | Bates |
| 6,179,831 B1 | 1/2001 | Bliweis |
| 6,183,435 B1 | 2/2001 | Bumbalough |
| 6,200,573 B1 | 3/2001 | Locke |
| 6,206,903 B1 | 3/2001 | Ramans |
| 6,216,573 B1 | 4/2001 | Moutafis |
| 6,217,543 B1 | 4/2001 | Anis |
| 6,217,860 B1 | 4/2001 | Woo |
| 6,228,046 B1 | 5/2001 | Brisken |
| 6,231,591 B1 | 5/2001 | Desai |
| 6,254,597 B1 | 7/2001 | Rizoiu |
| 6,296,639 B1 | 10/2001 | Truckai |
| 6,322,557 B1 | 11/2001 | Nikolaevich |
| 6,326,616 B1 | 12/2001 | Andrien, Jr. |
| 6,371,952 B1 | 4/2002 | Madhani |
| 6,375,635 B1 | 4/2002 | Moutafis |
| 6,378,525 B1 | 4/2002 | Beyar |
| 6,394,998 B1 | 5/2002 | Wallace |
| 6,398,792 B1 | 6/2002 | O'Connor |
| 6,405,078 B1 | 6/2002 | Moaddeb |
| 6,406,486 B1 | 6/2002 | De La Torre |
| 6,413,256 B1 | 7/2002 | Truckai |
| 6,425,877 B1 * | 7/2002 | Edwards ............ A61B 18/1477 606/41 |
| 6,436,107 B1 | 8/2002 | Wang |
| 6,440,061 B1 | 8/2002 | Wenner |
| 6,440,105 B1 | 8/2002 | Menne |
| 6,451,017 B1 | 9/2002 | Moutafis |
| 6,505,629 B1 | 1/2003 | Mikus |
| 6,508,823 B1 | 1/2003 | Gonon |
| 6,522,906 B1 | 2/2003 | Salisbury, Jr. |
| 6,524,270 B1 | 2/2003 | Bolmsjö |
| 6,554,793 B1 | 4/2003 | Pauker |
| 6,565,555 B1 | 5/2003 | Ryan |
| 6,572,578 B1 | 6/2003 | Blanchard |
| 6,577,891 B1 | 6/2003 | Jaross |
| 6,602,227 B1 | 8/2003 | Cimino |
| 6,607,524 B1 | 8/2003 | Labudde |
| 6,638,246 B1 | 10/2003 | Naimark |
| 6,671,581 B2 | 12/2003 | Niemeyer |
| 6,676,668 B2 | 1/2004 | Mercereau |
| 6,685,698 B2 | 2/2004 | Morley |
| 6,695,871 B1 | 2/2004 | Maki |
| 6,706,050 B1 | 3/2004 | Giannadakis |
| 6,720,745 B2 | 4/2004 | Lys |
| 6,736,784 B1 | 5/2004 | Menne |
| 6,763,259 B1 | 7/2004 | Hauger |
| 6,814,731 B2 | 11/2004 | Swanson |
| 6,821,275 B2 | 11/2004 | Truckai |
| 6,890,332 B2 | 5/2005 | Truckai |
| 6,905,475 B2 | 6/2005 | Hauschild |
| 6,923,805 B1 | 8/2005 | Lafontaine |
| 6,953,461 B2 | 10/2005 | McClurken |
| 6,960,182 B2 | 11/2005 | Moutafis |
| 6,986,764 B2 | 1/2006 | Davenport |
| 7,015,253 B2 | 3/2006 | Escandon |
| 7,087,061 B2 | 8/2006 | Chernenko |
| 7,115,100 B2 | 10/2006 | McRury |
| 7,122,017 B2 | 10/2006 | Moutafis |
| 7,163,875 B2 | 1/2007 | Richerzhagen |
| 7,228,165 B1 | 6/2007 | Sullivan |
| 7,282,055 B2 | 10/2007 | Tsuruta |
| 7,320,594 B1 | 1/2008 | Rizoiu |
| 7,326,054 B2 | 2/2008 | Todd |
| 7,344,528 B1 | 3/2008 | Tu |
| 7,351,193 B2 | 4/2008 | Forman |
| 7,556,632 B2 | 7/2009 | Zadno |
| 7,559,934 B2 | 7/2009 | Teague |
| 7,572,257 B2 | 8/2009 | Whayne |
| 7,594,900 B1 | 9/2009 | Nash |
| 7,725,214 B2 | 5/2010 | Diolaiti |
| 7,736,356 B2 | 6/2010 | Cooper |
| 7,882,841 B2 | 2/2011 | Aljuri |
| 7,883,475 B2 | 2/2011 | Dupont |
| 7,963,911 B2 | 6/2011 | Terliuc |
| 7,967,799 B2 | 6/2011 | Boukhny |
| 7,987,046 B1 | 7/2011 | Peterman |
| 8,002,713 B2 | 8/2011 | Heske |
| 8,038,598 B2 | 10/2011 | Khachi |
| 8,049,873 B2 | 11/2011 | Hauger |
| 8,092,397 B2 | 1/2012 | Wallace |
| 8,092,507 B2 | 1/2012 | Tomasello |
| 8,152,816 B2 | 4/2012 | Tuma |
| 8,187,173 B2 | 5/2012 | Miyoshi |
| 8,224,484 B2 | 7/2012 | Swarup |
| 8,229,188 B2 | 7/2012 | Rusko |
| 8,257,303 B2 | 9/2012 | Moll |
| 8,414,564 B2 | 4/2013 | Goldshleger |
| 8,419,723 B2 | 4/2013 | Shadduck |
| 8,480,595 B2 | 7/2013 | Speeg |

(56) References Cited

U.S. PATENT DOCUMENTS

| | | |
|---|---|---|
| 8,518,024 B2 | 8/2013 | Williams |
| 8,523,762 B2 | 9/2013 | Miyamoto |
| 8,540,748 B2 | 9/2013 | Murphy |
| 8,795,194 B2 | 8/2014 | Howard |
| 8,801,702 B2 * | 8/2014 | Hoey .................... A61B 18/04 606/41 |
| 8,814,921 B2 | 8/2014 | Aljuri |
| 8,820,603 B2 | 9/2014 | Shelton, IV |
| 8,827,948 B2 | 9/2014 | Romo |
| 8,882,660 B2 | 11/2014 | Phee |
| 8,945,163 B2 | 2/2015 | Voegele |
| 8,956,280 B2 | 2/2015 | Eversull |
| 9,144,461 B2 | 9/2015 | Kruecker |
| 9,173,713 B2 | 11/2015 | Hart |
| 9,232,959 B2 | 1/2016 | Aljuri |
| 9,232,960 B2 | 1/2016 | Aljuri |
| 9,237,902 B2 | 1/2016 | Aljuri |
| 9,254,123 B2 | 2/2016 | Alvarez |
| 9,277,969 B2 | 3/2016 | Brannan |
| 9,345,456 B2 | 5/2016 | Tsonton |
| 9,364,250 B2 | 6/2016 | Aljuri |
| 9,364,251 B2 | 6/2016 | Aljuri |
| 9,460,536 B2 | 10/2016 | Hasegawa |
| 9,504,604 B2 | 11/2016 | Alvarez |
| 9,510,852 B2 | 12/2016 | Aljuri |
| 9,510,853 B2 | 12/2016 | Aljuri |
| 9,561,083 B2 | 2/2017 | Yu |
| 9,592,042 B2 | 3/2017 | Titus |
| 9,597,152 B2 | 3/2017 | Schaeffer |
| 9,622,827 B2 | 4/2017 | Yu |
| 9,636,184 B2 | 5/2017 | Lee |
| 9,668,764 B2 | 6/2017 | Aljuri |
| 9,713,509 B2 | 7/2017 | Schuh |
| 9,727,963 B2 | 8/2017 | Mintz |
| 9,730,757 B2 | 8/2017 | Brudniok |
| 9,737,371 B2 | 8/2017 | Romo |
| 9,737,373 B2 | 8/2017 | Schuh |
| 9,744,335 B2 | 8/2017 | Jiang |
| 9,763,741 B2 | 9/2017 | Alvarez |
| 9,788,910 B2 | 10/2017 | Schuh |
| 9,844,412 B2 | 12/2017 | Bogusky |
| 9,848,904 B2 | 12/2017 | Aljuri |
| 9,867,635 B2 | 1/2018 | Alvarez |
| 9,867,636 B2 | 1/2018 | McLeod |
| 9,918,681 B2 | 3/2018 | Wallace |
| 9,931,025 B1 | 4/2018 | Graetzel |
| 9,931,445 B2 | 4/2018 | Pustilnik |
| 9,949,749 B2 | 4/2018 | Noonan |
| 9,955,986 B2 | 5/2018 | Shah |
| 9,962,228 B2 | 5/2018 | Schuh |
| 9,980,785 B2 | 5/2018 | Schuh |
| 9,993,313 B2 | 6/2018 | Schuh |
| 10,016,900 B1 | 7/2018 | Meyer |
| 10,022,192 B1 | 7/2018 | Ummalaneni |
| 10,080,576 B2 | 9/2018 | Romo |
| 10,136,959 B2 | 11/2018 | Mintz |
| 10,145,747 B1 | 12/2018 | Lin |
| 10,149,720 B2 | 12/2018 | Romo |
| 10,159,532 B1 | 12/2018 | Ummalaneni |
| 10,159,533 B2 | 12/2018 | Moll |
| 10,169,875 B2 | 1/2019 | Mintz |
| 10,226,298 B2 | 3/2019 | Ourselin |
| 10,231,867 B2 | 3/2019 | Alvarez |
| 10,251,665 B2 * | 4/2019 | Aljuri .................... A61B 18/24 |
| 10,321,931 B2 | 6/2019 | Aljuri |
| 10,342,615 B2 * | 7/2019 | Aljuri .................... A61B 18/20 |
| 10,423,757 B2 | 9/2019 | Kruecker |
| 10,448,956 B2 | 10/2019 | Gordon |
| 10,482,599 B2 | 11/2019 | Mintz |
| 10,517,692 B2 | 12/2019 | Eyre |
| 10,524,866 B2 | 1/2020 | Srinivasan |
| 10,639,114 B2 | 5/2020 | Schuh |
| 10,653,438 B2 | 5/2020 | Aljuri |
| 10,980,669 B2 | 4/2021 | Alvarez |
| 11,033,330 B2 | 6/2021 | Aljuri |
| 11,172,986 B2 | 11/2021 | Aljuri |
| 11,278,451 B2 | 3/2022 | Andrews |
| 11,350,964 B2 * | 6/2022 | Aljuri .................... A61B 18/24 |
| 11,464,536 B2 | 10/2022 | Aljuri |
| 11,478,269 B2 | 10/2022 | Aljuri |
| 11,737,776 B2 | 8/2023 | Aljuri |
| 11,759,258 B2 | 9/2023 | Aljuri |
| 2001/0048942 A1 | 12/2001 | Weisman |
| 2002/0010502 A1 | 1/2002 | Trachtenberg |
| 2002/0019644 A1 | 2/2002 | Hastings |
| 2002/0022869 A1 | 2/2002 | Hareyama |
| 2002/0040220 A1 | 4/2002 | Zvuloni |
| 2002/0042620 A1 | 4/2002 | Julian |
| 2002/0077550 A1 | 6/2002 | Rabiner |
| 2002/0111608 A1 | 8/2002 | Baerveldt |
| 2002/0111617 A1 * | 8/2002 | Cosman ............. A61B 18/1485 606/41 |
| 2002/0111621 A1 | 8/2002 | Wallace |
| 2002/0128637 A1 | 9/2002 | Von Der Heide |
| 2002/0183735 A1 | 12/2002 | Edwards |
| 2003/0004455 A1 | 1/2003 | Kadziauskas |
| 2003/0036768 A1 | 2/2003 | Hutchins |
| 2003/0040681 A1 | 2/2003 | Ng |
| 2003/0060813 A1 | 3/2003 | Loeb |
| 2003/0060819 A1 | 3/2003 | McGovern |
| 2003/0065321 A1 * | 4/2003 | Carmel ............. A61B 18/1402 606/41 |
| 2003/0065358 A1 | 4/2003 | Frecker |
| 2003/0073902 A1 | 4/2003 | Hauschild |
| 2003/0073920 A1 | 4/2003 | Smits |
| 2003/0109877 A1 | 6/2003 | Morley |
| 2003/0109889 A1 | 6/2003 | Mercereau |
| 2003/0135205 A1 | 7/2003 | Davenport |
| 2003/0139041 A1 | 7/2003 | Leclair |
| 2003/0158545 A1 | 8/2003 | Hovda |
| 2003/0199860 A1 | 10/2003 | Loeb |
| 2003/0208189 A1 | 11/2003 | Payman |
| 2003/0216722 A1 | 11/2003 | Swanson |
| 2004/0030349 A1 | 2/2004 | Boukhny |
| 2004/0059216 A1 | 3/2004 | Vetter |
| 2004/0097829 A1 | 5/2004 | McRury |
| 2004/0133254 A1 | 7/2004 | Sterzer |
| 2004/0143253 A1 | 7/2004 | Vanney |
| 2004/0153093 A1 | 8/2004 | Donovan |
| 2004/0158261 A1 | 8/2004 | Vu |
| 2004/0186349 A1 | 9/2004 | Ewers |
| 2004/0193146 A1 | 9/2004 | Lee |
| 2004/0210116 A1 | 10/2004 | Nakao |
| 2004/0215294 A1 | 10/2004 | Littrup |
| 2004/0230211 A1 | 11/2004 | Moutafis |
| 2004/0253079 A1 | 12/2004 | Sanchez |
| 2004/0254422 A1 | 12/2004 | Singh |
| 2005/0004516 A1 | 1/2005 | Vanney |
| 2005/0010205 A1 | 1/2005 | Hovda |
| 2005/0033270 A1 | 2/2005 | Ramans |
| 2005/0054900 A1 | 3/2005 | Mawn |
| 2005/0054994 A1 | 3/2005 | Cioanta |
| 2005/0070844 A1 | 3/2005 | Chow |
| 2005/0131399 A1 | 6/2005 | Loeb |
| 2005/0159645 A1 | 7/2005 | Bertolero |
| 2005/0159676 A1 | 7/2005 | Taylor |
| 2005/0165383 A1 | 7/2005 | Eshel |
| 2005/0192652 A1 | 9/2005 | Cioanta |
| 2005/0240178 A1 | 10/2005 | Morley |
| 2005/0256517 A1 | 11/2005 | Boutoussov |
| 2005/0261705 A1 | 11/2005 | Gist |
| 2005/0288639 A1 | 12/2005 | Hibner |
| 2005/0288665 A1 | 12/2005 | Woloszko |
| 2006/0015133 A1 | 1/2006 | Grayzel |
| 2006/0030787 A1 | 2/2006 | Quay |
| 2006/0058813 A1 | 3/2006 | Teague |
| 2006/0089626 A1 | 4/2006 | Vlegele |
| 2006/0116693 A1 | 6/2006 | Weisenburgh, II |
| 2006/0118495 A1 | 6/2006 | Kondratalv |
| 2006/0129125 A1 | 6/2006 | Copa |
| 2006/0135963 A1 | 6/2006 | Kick |
| 2006/0149193 A1 | 7/2006 | Hall |
| 2006/0156875 A1 | 7/2006 | McRury |
| 2006/0167416 A1 | 7/2006 | Mathis |

(56) References Cited

U.S. PATENT DOCUMENTS

| | | |
|---|---|---|
| 2006/0178670 A1 | 8/2006 | Woloszko |
| 2006/0189891 A1 | 8/2006 | Waxman |
| 2006/0258938 A1 | 11/2006 | Hoffman |
| 2006/0293646 A1 | 12/2006 | Whayne |
| 2007/0005002 A1 | 1/2007 | Millman |
| 2007/0016164 A1 | 1/2007 | Dudney |
| 2007/0025874 A1 | 2/2007 | Ophardt |
| 2007/0027443 A1 | 2/2007 | Rose |
| 2007/0027534 A1 | 2/2007 | Bergheim |
| 2007/0032906 A1 | 2/2007 | Sutherland |
| 2007/0038112 A1 | 2/2007 | Taylor |
| 2007/0106304 A1 | 5/2007 | Hammack |
| 2007/0129680 A1 | 6/2007 | Hagg |
| 2007/0135763 A1 | 6/2007 | Musbach |
| 2007/0135803 A1 | 6/2007 | Belson |
| 2007/0185474 A1 | 8/2007 | Nahen |
| 2007/0208375 A1 | 9/2007 | Nishizawa |
| 2007/0213668 A1 | 9/2007 | Spitz |
| 2007/0230757 A1 | 10/2007 | Trachtenberg |
| 2007/0239153 A1 | 10/2007 | Hodorek |
| 2007/0239178 A1 | 10/2007 | Weitzner |
| 2007/0250111 A1 | 10/2007 | Lu |
| 2007/0278195 A1 | 12/2007 | Richerzhagen |
| 2007/0299427 A1 | 12/2007 | Yeung |
| 2008/0004603 A1 | 1/2008 | Larkin |
| 2008/0015566 A1 | 1/2008 | Livneh |
| 2008/0021440 A1 | 1/2008 | Solomon |
| 2008/0027420 A1 | 1/2008 | Wang |
| 2008/0032251 A1 | 2/2008 | Chou |
| 2008/0033467 A1 | 2/2008 | Miyamoto |
| 2008/0038124 A1 | 2/2008 | Kuehner |
| 2008/0046122 A1 | 2/2008 | Manzo |
| 2008/0065103 A1 | 3/2008 | Cooper |
| 2008/0065109 A1 | 3/2008 | Larkin |
| 2008/0065111 A1 | 3/2008 | Blumenkranz |
| 2008/0082091 A1 | 4/2008 | Rubtsov |
| 2008/0097293 A1 | 4/2008 | Chin |
| 2008/0097470 A1 | 4/2008 | Gruber |
| 2008/0108934 A1 | 5/2008 | Berlin |
| 2008/0114341 A1 | 5/2008 | Thyzel |
| 2008/0125698 A1 | 5/2008 | Gerg |
| 2008/0154258 A1 | 6/2008 | Chang |
| 2008/0177285 A1 | 7/2008 | Brock |
| 2008/0187101 A1 | 8/2008 | Gertner |
| 2008/0188868 A1 | 8/2008 | Weitzner |
| 2008/0196533 A1 | 8/2008 | Bergamasco |
| 2008/0221602 A1 | 9/2008 | Kuehner |
| 2008/0228104 A1 | 9/2008 | Uber |
| 2008/0243157 A1 | 10/2008 | Klein |
| 2008/0249526 A1 | 10/2008 | Knowlton |
| 2008/0267468 A1 | 10/2008 | Geiger |
| 2009/0012507 A1 | 1/2009 | Culbertson |
| 2009/0018533 A1 | 1/2009 | Perkins |
| 2009/0030370 A1 | 1/2009 | Nishtala |
| 2009/0030446 A1 | 1/2009 | Measamer |
| 2009/0036900 A1 | 2/2009 | Moll |
| 2009/0043305 A1 | 2/2009 | Brodbeck |
| 2009/0060764 A1 | 3/2009 | Mitzlaff |
| 2009/0062602 A1 | 3/2009 | Rosenberg |
| 2009/0082634 A1 | 3/2009 | Kathrani |
| 2009/0088774 A1 | 4/2009 | Swarup |
| 2009/0088775 A1 | 4/2009 | Swarup |
| 2009/0105723 A1 | 4/2009 | Dillinger |
| 2009/0131885 A1 | 5/2009 | Akahoshi |
| 2009/0149712 A1 | 6/2009 | Fischer |
| 2009/0157114 A1 | 6/2009 | Fischer |
| 2009/0161827 A1 | 6/2009 | Gertner |
| 2009/0171271 A1 | 7/2009 | Webster |
| 2009/0221998 A1 | 9/2009 | Epstein |
| 2009/0227998 A1 | 9/2009 | Aljuri |
| 2009/0248041 A1 | 10/2009 | Williams |
| 2009/0248043 A1 | 10/2009 | Tierney |
| 2009/0254075 A1 | 10/2009 | Paz |
| 2009/0264878 A1 | 10/2009 | Carmel |
| 2009/0268015 A1 | 10/2009 | Scott |
| 2009/0270760 A1 | 10/2009 | Leimbach |
| 2009/0287045 A1 | 11/2009 | Mitelberg |
| 2009/0287188 A1 | 11/2009 | Golden |
| 2009/0299352 A1 | 12/2009 | Zerfas |
| 2009/0312768 A1 | 12/2009 | Hawkins |
| 2009/0326322 A1 | 12/2009 | Diolaiti |
| 2010/0004642 A1 | 1/2010 | Lumpkin |
| 2010/0010504 A1 | 1/2010 | Simaan |
| 2010/0011900 A1 | 1/2010 | Burbank |
| 2010/0011901 A1 | 1/2010 | Burbank |
| 2010/0036294 A1 | 2/2010 | Mantell |
| 2010/0073150 A1 | 3/2010 | Olson |
| 2010/0076269 A1 | 3/2010 | Makower |
| 2010/0082017 A1 | 4/2010 | Zickler |
| 2010/0114115 A1 | 5/2010 | Schlesinger |
| 2010/0143778 A1 | 6/2010 | Huang |
| 2010/0145254 A1 | 6/2010 | Shadduck |
| 2010/0179522 A1 | 7/2010 | Companion |
| 2010/0179632 A1 | 7/2010 | Bruszewski |
| 2010/0204605 A1 | 8/2010 | Blakley |
| 2010/0204646 A1 | 8/2010 | Plicchi |
| 2010/0217235 A1 | 8/2010 | Thorstenson |
| 2010/0225209 A1 | 9/2010 | Goldberg |
| 2010/0228191 A1 | 9/2010 | Alvarez |
| 2010/0228249 A1 | 9/2010 | Mohr |
| 2010/0268211 A1 | 10/2010 | Manwaring |
| 2010/0280320 A1 | 11/2010 | Alvarez |
| 2010/0280525 A1 | 11/2010 | Alvarez |
| 2010/0312141 A1 | 12/2010 | Keast |
| 2010/0331858 A1 | 12/2010 | Simaan |
| 2011/0009779 A1 | 1/2011 | Romano |
| 2011/0015483 A1 | 1/2011 | Barbagli |
| 2011/0015648 A1 | 1/2011 | Alvarez |
| 2011/0018439 A1 | 1/2011 | Fabbri |
| 2011/0028887 A1 | 2/2011 | Fischer |
| 2011/0040404 A1 | 2/2011 | Diolaiti |
| 2011/0046441 A1 | 2/2011 | Wiltshire |
| 2011/0054315 A1 | 3/2011 | Roberts |
| 2011/0071541 A1 | 3/2011 | Prisco |
| 2011/0071543 A1 | 3/2011 | Prisco |
| 2011/0104800 A1 | 5/2011 | Kensy |
| 2011/0106102 A1 | 5/2011 | Balicki |
| 2011/0106146 A1 | 5/2011 | Jeong |
| 2011/0125165 A1 | 5/2011 | Simaan |
| 2011/0144632 A1 | 6/2011 | Bourne |
| 2011/0152880 A1 | 6/2011 | Alvarez |
| 2011/0160713 A1 | 6/2011 | Neuberger |
| 2011/0167611 A1 | 7/2011 | Williams |
| 2011/0184291 A1 | 7/2011 | Okamura |
| 2011/0184391 A1 | 7/2011 | Aljuri |
| 2011/0213362 A1 | 9/2011 | Cunningham |
| 2011/0224660 A1 | 9/2011 | Neuberger |
| 2011/0238064 A1 | 9/2011 | Williams |
| 2011/0245757 A1 | 10/2011 | Myntti |
| 2011/0251578 A1 | 10/2011 | Peyman |
| 2011/0257641 A1 | 10/2011 | Hastings |
| 2011/0276085 A1 | 11/2011 | Krzyzanowski |
| 2011/0306836 A1 | 12/2011 | Ohline |
| 2011/0313343 A1 | 12/2011 | Milutinovic |
| 2012/0046605 A1 | 2/2012 | Uchida |
| 2012/0069167 A1 | 3/2012 | Liu |
| 2012/0071719 A1 | 3/2012 | Shanley |
| 2012/0138586 A1 | 6/2012 | Webster |
| 2012/0157841 A1 | 6/2012 | Glaenzer |
| 2012/0209315 A1 | 8/2012 | Amat Girbau |
| 2012/0232342 A1 | 9/2012 | Reydel |
| 2012/0253277 A1 | 10/2012 | Tah |
| 2012/0253332 A1 | 10/2012 | Moll |
| 2012/0259320 A1 | 10/2012 | Loesel |
| 2012/0283747 A1 | 11/2012 | Popovic |
| 2012/0296318 A1 | 11/2012 | Wellhoefer |
| 2012/0296394 A1 | 11/2012 | Culbertson |
| 2013/0006144 A1 | 1/2013 | Clancy |
| 2013/0035537 A1 | 2/2013 | Wallace |
| 2013/0053877 A1 | 2/2013 | Benmaamer |
| 2013/0066136 A1 | 3/2013 | Palese |
| 2013/0085442 A1 | 4/2013 | Shtul |
| 2013/0085482 A1 | 4/2013 | Van Valen |
| 2013/0085484 A1 | 4/2013 | Van Valen |

(56) References Cited

U.S. PATENT DOCUMENTS

| | | |
|---|---|---|
| 2013/0085486 A1 | 4/2013 | Boutoussov |
| 2013/0096422 A1 | 4/2013 | Boctor |
| 2013/0096574 A1 | 4/2013 | Kang |
| 2013/0110042 A1 | 5/2013 | Humphreys |
| 2013/0110107 A1 | 5/2013 | Smith |
| 2013/0116716 A1 | 5/2013 | Bahls |
| 2013/0144116 A1 | 6/2013 | Cooper |
| 2013/0144274 A1 | 6/2013 | Stefanchik |
| 2013/0144395 A1 | 6/2013 | Stefanchik |
| 2013/0190796 A1 | 7/2013 | Tilson |
| 2013/0225997 A1 | 8/2013 | Dillard |
| 2013/0226161 A1 | 8/2013 | Hickenbotham |
| 2013/0253267 A1 | 9/2013 | Collins |
| 2013/0253484 A1 | 9/2013 | Aljuri |
| 2013/0253488 A1 | 9/2013 | Aljuri |
| 2013/0261540 A1 | 10/2013 | Crank |
| 2013/0267889 A1 | 10/2013 | Aljuri |
| 2013/0303876 A1 | 11/2013 | Gelfand |
| 2013/0310819 A1 | 11/2013 | Wolfgang |
| 2013/0345686 A1 | 12/2013 | Brown |
| 2014/0005681 A1 | 1/2014 | Gee |
| 2014/0012276 A1 | 1/2014 | Alvarez |
| 2014/0039681 A1 | 2/2014 | Gene |
| 2014/0046308 A1 | 2/2014 | Bischoff |
| 2014/0051985 A1 | 2/2014 | Fan |
| 2014/0058361 A1 | 2/2014 | Gordon |
| 2014/0058365 A1 | 2/2014 | Bille |
| 2014/0058404 A1 | 2/2014 | Hammack |
| 2014/0058428 A1 | 2/2014 | Christopher |
| 2014/0100445 A1 | 4/2014 | Stenzel |
| 2014/0142591 A1 | 5/2014 | Alvarez |
| 2014/0163318 A1 | 6/2014 | Swanstrom |
| 2014/0193833 A1 | 7/2014 | Srivastava |
| 2014/0194859 A1 | 7/2014 | Ianchulev |
| 2014/0194905 A1 | 7/2014 | Kappel |
| 2014/0243849 A1 | 8/2014 | Saglam |
| 2014/0275956 A1 | 9/2014 | Fan |
| 2014/0276594 A1 | 9/2014 | Tanner |
| 2014/0276723 A1 | 9/2014 | Parihar |
| 2014/0276933 A1 | 9/2014 | Hart |
| 2014/0276956 A1 | 9/2014 | Crainich |
| 2014/0309649 A1 | 10/2014 | Alvarez |
| 2014/0309655 A1 | 10/2014 | Gal |
| 2014/0316203 A1 | 10/2014 | Carroux |
| 2014/0357984 A1 | 12/2014 | Wallace |
| 2014/0364870 A1 | 12/2014 | Alvarez |
| 2014/0379000 A1 | 12/2014 | Romo |
| 2015/0025539 A1 | 1/2015 | Alvarez |
| 2015/0045777 A1 | 2/2015 | Aljuri |
| 2015/0051592 A1 | 2/2015 | Kintz |
| 2015/0057646 A1 | 2/2015 | Aljuri |
| 2015/0080879 A1 | 3/2015 | Trees |
| 2015/0088107 A1 | 3/2015 | Aljuri |
| 2015/0088110 A1 | 3/2015 | Aljuri |
| 2015/0101442 A1 | 4/2015 | Romo |
| 2015/0119638 A1 | 4/2015 | Yu |
| 2015/0127045 A1 | 5/2015 | Prestel |
| 2015/0133960 A1 | 5/2015 | Lohmeier |
| 2015/0164522 A1 | 6/2015 | Budiman |
| 2015/0164594 A1 | 6/2015 | Romo |
| 2015/0164595 A1 | 6/2015 | Bogusky |
| 2015/0164596 A1 | 6/2015 | Romo |
| 2015/0201917 A1 | 7/2015 | Snow |
| 2015/0202085 A1 | 7/2015 | Lemonis |
| 2015/0313666 A1 | 11/2015 | Aljuri |
| 2015/0314110 A1 | 11/2015 | Park |
| 2015/0335344 A1 | 11/2015 | Aljuri |
| 2015/0335480 A1 | 11/2015 | Alvarez |
| 2016/0001038 A1 | 1/2016 | Romo |
| 2016/0022289 A1 | 1/2016 | Wan |
| 2016/0022466 A1 | 1/2016 | Pedtke |
| 2016/0030073 A1 | 2/2016 | Isakov |
| 2016/0045208 A1 | 2/2016 | Ciulla |
| 2016/0051318 A1 | 2/2016 | Manzo |
| 2016/0066935 A1 | 3/2016 | Nguyen |
| 2016/0074059 A1 | 3/2016 | Aljuri |
| 2016/0143778 A1 | 5/2016 | Aljuri |
| 2016/0151122 A1 | 6/2016 | Alvarez |
| 2016/0158490 A1 | 6/2016 | Leeflang |
| 2016/0183841 A1 | 6/2016 | Duindam |
| 2016/0199984 A1 | 7/2016 | Lohmeier |
| 2016/0228141 A1 | 8/2016 | Aljuri |
| 2016/0235495 A1 | 8/2016 | Wallace |
| 2016/0249932 A1 | 9/2016 | Rogers |
| 2016/0270865 A1 | 9/2016 | Landey |
| 2016/0279394 A1 | 9/2016 | Moll |
| 2016/0287279 A1 | 10/2016 | Bovay |
| 2016/0296294 A1 | 10/2016 | Moll |
| 2016/0303743 A1 | 10/2016 | Rockrohr |
| 2016/0331358 A1 | 11/2016 | Gordon |
| 2016/0367324 A1 | 12/2016 | Sato |
| 2016/0374541 A1 | 12/2016 | Agrawal |
| 2017/0007337 A1 | 1/2017 | Dan |
| 2017/0049471 A1 | 2/2017 | Gaffney |
| 2017/0065227 A1 | 3/2017 | Marrs |
| 2017/0095234 A1 | 4/2017 | Prisco |
| 2017/0095295 A1 | 4/2017 | Overmyer |
| 2017/0100199 A1 | 4/2017 | Yu |
| 2017/0119413 A1 | 5/2017 | Romo |
| 2017/0119481 A1 | 5/2017 | Romo |
| 2017/0135706 A1 | 5/2017 | Frey |
| 2017/0151416 A1 | 6/2017 | Kutikov |
| 2017/0165011 A1 | 6/2017 | Bovay |
| 2017/0172553 A1 | 6/2017 | Chaplin |
| 2017/0172673 A1 | 6/2017 | Yu |
| 2017/0202627 A1 | 7/2017 | Sramek |
| 2017/0209073 A1 | 7/2017 | Sramek |
| 2017/0245878 A1 | 8/2017 | Aljuri |
| 2017/0252096 A1 | 9/2017 | Felder |
| 2017/0265923 A1 | 9/2017 | Privitera |
| 2017/0273797 A1 | 9/2017 | Gordon |
| 2017/0290631 A1 | 10/2017 | Lee |
| 2017/0319289 A1 | 11/2017 | Neff |
| 2017/0333679 A1 | 11/2017 | Jiang |
| 2017/0340396 A1 | 11/2017 | Romo |
| 2017/0365055 A1 | 12/2017 | Mintz |
| 2017/0367782 A1 | 12/2017 | Schuh |
| 2018/0000563 A1 | 1/2018 | Shanjani |
| 2018/0025666 A1 | 1/2018 | Ho |
| 2018/0028261 A1 | 2/2018 | Chen |
| 2018/0049824 A1 | 2/2018 | Harris |
| 2018/0177383 A1 | 6/2018 | Noonan |
| 2018/0177556 A1 | 6/2018 | Noonan |
| 2018/0193049 A1 | 7/2018 | Heck |
| 2018/0214011 A1 | 8/2018 | Graetzel |
| 2018/0221038 A1 | 8/2018 | Noonan |
| 2018/0221039 A1 | 8/2018 | Shah |
| 2018/0250083 A1 | 9/2018 | Schuh |
| 2018/0271616 A1 | 9/2018 | Schuh |
| 2018/0279852 A1 | 10/2018 | Rafii-Tari |
| 2018/0280660 A1 | 10/2018 | Landey |
| 2018/0289243 A1 | 10/2018 | Landey |
| 2018/0289431 A1 | 10/2018 | Draper |
| 2018/0296285 A1 | 10/2018 | Simi |
| 2018/0318011 A1 | 11/2018 | Leibinger |
| 2018/0325499 A1 | 11/2018 | Landey |
| 2018/0333044 A1 | 11/2018 | Jenkins |
| 2018/0360435 A1 | 12/2018 | Romo |
| 2019/0000559 A1 | 1/2019 | Berman |
| 2019/0000560 A1 | 1/2019 | Berman |
| 2019/0000566 A1 | 1/2019 | Graetzel |
| 2019/0000568 A1 | 1/2019 | Connolly |
| 2019/0000576 A1 | 1/2019 | Mintz |
| 2019/0083183 A1 | 3/2019 | Moll |
| 2019/0099231 A1 | 4/2019 | Bruehwiler |
| 2019/0105776 A1 | 4/2019 | Ho |
| 2019/0105785 A1 | 4/2019 | Meyer |
| 2019/0107454 A1 | 4/2019 | Lin |
| 2019/0110839 A1 | 4/2019 | Rafii-Tari |
| 2019/0110843 A1 | 4/2019 | Ummalaneni |
| 2019/0151148 A1 | 5/2019 | Alvarez |
| 2019/0167366 A1 | 6/2019 | Ummalaneni |
| 2019/0175009 A1 | 6/2019 | Mintz |
| 2019/0175062 A1 | 6/2019 | Rafii-Tari |

(56) References Cited

U.S. PATENT DOCUMENTS

| | | |
|---|---|---|
| 2019/0175287 A1 | 6/2019 | Hill |
| 2019/0175799 A1 | 6/2019 | Hsu |
| 2019/0183585 A1 | 6/2019 | Rafii-Tari |
| 2019/0183587 A1 | 6/2019 | Rafii-Tari |
| 2019/0201214 A1 | 7/2019 | Miller |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz |
| 2019/0231426 A1 | 8/2019 | Aljuri |
| 2019/0239890 A1 | 8/2019 | Stokes |
| 2019/0246882 A1 | 8/2019 | Graetzel |
| 2019/0247071 A1 | 8/2019 | Aljuri |
| 2019/0262086 A1 | 8/2019 | Connolly |
| 2019/0269468 A1 | 9/2019 | Hsu |
| 2019/0274764 A1 | 9/2019 | Romo |
| 2019/0290109 A1 | 9/2019 | Agrawal |
| 2019/0298160 A1 | 10/2019 | Ummalaneni |
| 2019/0298460 A1 | 10/2019 | Al-Jadda |
| 2019/0298465 A1 | 10/2019 | Chin |
| 2019/0314616 A1 | 10/2019 | Moll |
| 2019/0328213 A1 | 10/2019 | Landey |
| 2019/0336238 A1 | 11/2019 | Yu |
| 2019/0365209 A1 | 12/2019 | Ye |
| 2019/0365479 A1 | 12/2019 | Rafii-Tari |
| 2019/0365486 A1 | 12/2019 | Srinivasan |
| 2019/0374297 A1 | 12/2019 | Wallace |
| 2019/0375383 A1 | 12/2019 | Auer |
| 2019/0380787 A1 | 12/2019 | Ye |
| 2019/0380797 A1 | 12/2019 | Yu |
| 2020/0000530 A1 | 1/2020 | Defonzo |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054408 A1 | 2/2020 | Schuh |
| 2020/0060516 A1 | 2/2020 | Baez, Jr. |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0163726 A1 | 5/2020 | Tanner |
| 2020/0323590 A1 | 10/2020 | Aljuri |
| 2020/0330118 A1 | 10/2020 | Aljuri |
| 2020/0375622 A1 | 12/2020 | Aljuri |
| 2021/0128189 A1 | 5/2021 | Aljuri |
| 2021/0251646 A1 | 8/2021 | Aljuri |
| 2021/0251690 A1 | 8/2021 | Aljuri |
| 2021/0298954 A1 | 9/2021 | Alvarez |
| 2021/0307826 A1 | 10/2021 | Aljuri |
| 2022/0096112 A1 | 3/2022 | Aljuri |
| 2023/0063051 A1 | 3/2023 | Aljuri |
| 2024/0032958 A1 | 2/2024 | Aljuri |

FOREIGN PATENT DOCUMENTS

| | | |
|---|---|---|
| CN | 1725992 A | 1/2006 |
| CN | 101108133 A | 1/2008 |
| CN | 101108138 A | 1/2008 |
| CN | 101394877 A | 3/2009 |
| CN | 101443069 A | 5/2009 |
| CN | 100515347 C | 7/2009 |
| CN | 101902950 A | 12/2010 |
| CN | 102724939 A | 10/2012 |
| CN | 102905633 | 1/2013 |
| CN | 103298414 A | 9/2013 |
| CN | 205729413 A | 11/2016 |
| CN | 205729413 U | 11/2016 |
| DE | 9200447 | 4/1992 |
| DE | 9200447 U1 | 5/1992 |
| EP | 0598984 A1 | 6/1994 |
| EP | 0657150 | 6/1995 |
| EP | 0821916 A2 | 2/1998 |
| EP | 1075853 A2 | 2/2001 |
| EP | 1321106 A1 | 6/2003 |
| EP | 1486900 | 12/2004 |
| EP | 1683495 | 7/2006 |
| EP | 1849423 A2 | 10/2007 |
| EP | 3188667 A1 | 7/2017 |
| IN | 102238921 A | 11/2011 |
| JP | S61263444 A | 11/1986 |
| JP | S62117548 A | 5/1987 |
| JP | H029241 A | 1/1990 |
| JP | 05076540 | 3/1993 |
| JP | H0576540 | 3/1993 |
| JP | 6509241 A | 10/1994 |
| JP | H06509241 A | 10/1994 |
| JP | 3476878 B2 | 5/1995 |
| JP | H07136173 A | 5/1995 |
| JP | H09505759 A | 6/1997 |
| JP | H09224951 A | 9/1997 |
| JP | H11332880 A | 12/1999 |
| JP | 2000511089 | 8/2000 |
| JP | 2001046528 | 2/2001 |
| JP | 2001046528 A | 2/2001 |
| JP | 2001509038 A | 7/2001 |
| JP | 2001512358 A | 8/2001 |
| JP | 3349716 | 11/2002 |
| JP | 2003000713 A | 1/2003 |
| JP | 2003506131 A | 2/2003 |
| JP | 3476878 | 12/2003 |
| JP | 2004105707 A | 4/2004 |
| JP | 2004530477 A | 10/2004 |
| JP | 2005523741 A | 8/2005 |
| JP | 2005270464 A | 10/2005 |
| JP | 2006122307 A | 5/2006 |
| JP | 2006271691 A | 10/2006 |
| JP | 2007020837 A | 2/2007 |
| JP | 2007209465 A | 8/2007 |
| JP | 2009500126 | 1/2009 |
| JP | 2009502304 A | 1/2009 |
| JP | 2009518134 A | 5/2009 |
| JP | 2010514541 A | 5/2010 |
| JP | 2010520801 A | 6/2010 |
| JP | 2011067330 | 4/2011 |
| JP | 2011514211 A | 5/2011 |
| WO | 9004363 A1 | 5/1990 |
| WO | 9210142 A1 | 6/1992 |
| WO | 1992010142 A1 | 6/1992 |
| WO | 9214411 | 9/1992 |
| WO | 1993012446 A1 | 6/1993 |
| WO | 1993015664 A1 | 8/1993 |
| WO | 1994026185 A1 | 11/1994 |
| WO | 9640476 A1 | 12/1996 |
| WO | 1996039952 A1 | 12/1996 |
| WO | 1996040476 A1 | 12/1996 |
| WO | 9729803 A1 | 8/1997 |
| WO | 1997029803 A1 | 8/1997 |
| WO | 1998018388 A1 | 5/1998 |
| WO | 9956907 A1 | 11/1999 |
| WO | 1999056907 A1 | 11/1999 |
| WO | 2000059394 A1 | 10/2000 |
| WO | 0150966 | 7/2001 |
| WO | 2001049195 A1 | 7/2001 |
| WO | 2002091935 A1 | 11/2002 |
| WO | 03088833 A1 | 10/2003 |
| WO | 03096871 A1 | 11/2003 |
| WO | 2004004914 | 1/2004 |
| WO | 2004028592 A1 | 4/2004 |
| WO | 2004080529 A2 | 9/2004 |
| WO | 2004105849 A1 | 12/2004 |
| WO | 2006066160 A1 | 6/2006 |
| WO | 2007008700 | 1/2007 |
| WO | 2007011302 A1 | 1/2007 |
| WO | 2007114917 | 10/2007 |
| WO | 2007136984 | 11/2007 |
| WO | 2008036304 | 3/2008 |
| WO | 2008036305 | 3/2008 |
| WO | 2008049898 | 5/2008 |

(56) References Cited

FOREIGN PATENT DOCUMENTS

| | | | |
|---|---|---|---|
| WO | 2008083407 | A1 | 7/2008 |
| WO | 2009111736 | A1 | 9/2009 |
| WO | 2009152613 | A1 | 12/2009 |
| WO | 2010054237 | | 5/2010 |
| WO | 2010144419 | A2 | 12/2010 |
| WO | 2011097505 | | 8/2011 |
| WO | 2011097505 | A1 | 8/2011 |
| WO | 2011100753 | A2 | 8/2011 |
| WO | 2011141775 | A1 | 11/2011 |
| WO | 2011161218 | A1 | 12/2011 |
| WO | 2012040233 | | 3/2012 |
| WO | 2013009576 | A1 | 1/2013 |
| WO | 2013053614 | | 4/2013 |
| WO | 2013107468 | A1 | 7/2013 |
| WO | 2013130895 | A1 | 9/2013 |
| WO | 2014127242 | | 8/2014 |
| WO | 2015200538 | A1 | 12/2015 |
| WO | 2016004071 | A1 | 1/2016 |
| WO | 2016037132 | A1 | 3/2016 |
| WO | 2017114855 | A1 | 7/2017 |
| WO | 2018069679 | A1 | 4/2018 |
| WO | 2019137665 | | 7/2019 |

OTHER PUBLICATIONS

Botto et al., "Electrovaporization of the Prostate with the Gyrus Device," J. Endourol. (Apr. 2001) 15(3):313-316.
Ehlers, et al., "Integration of a spectral domain optical coherence tomography system into a surgical microscope for intraoperative imaging." Investigative Ophthalmology and Visual Science (2011); 52(6): 3153-3159.
Hillegersberg et al., "Water-jet-cooled Nd:YAG laser coagulation: selective destruction of rat liver metastases," Lasers Surg Med. 1991; 11(5):445-454. [Abstract Only].
International Search Report and Written Opinion for International Application No. PCT/US2011/023781, 12 pages (Mar. 31, 2011).
International Search Report and Written Opinion of International Application No. PCT/US08/50051, 10 pages (May 21, 2008).
Jian, et al. The Development of the Water Jet Scalpel With Air Pressure. Trans. ASME (Jun. 2001) 123(2):246-248.
Nishimura, et al. Similarity Law on Shedding Frequency of Cavitation Cloud Induced by a Cavitating Jet. Journal of Fluid Science and Technology, vol. 7, No. 3, 2012, pp. 405-420.
Pitcher, et al., "Robotic Eye Surgery: Past, Present, and Future". Journal of Computer Science and Systems Biology (2012); S3, 4 pages.
Prajapati, et al., Pluripotent Stem Cell within the Prostate could be Responsible for Benign Prostate Hyperplasia in Human, J Stem Cell Res Ther2014, 4:1.
Prajapati, et al., Prostate Stem Cells in the Development of Benign Prostate Hyperplasia and Prostate Cancer: Emerging Role and Concepts, Biomed Res Int 2013; 2013:107954.
Richerzhagen et al., "Water Jet Guided Laser Cutting: a Powerful Hybrid Technology for Fine Cutting and Grooving," Proceedings of the 2004 Advanced Laser Applications Conference and Exposition, Ann Arbor, Michigan, Sep. 20-22, 2004, ALAC 2004, 2:175-182; retrieved from the Internet <http://www.synova.ch/pdf/ALAC04.pdf>.
Sander et al., "The water jet-guided Nd:YAG laser in the treatment of gastroduodenal ulcer with a visible vessel. A randomized controlled and prospective study," Endoscopy. Sep. 1989; 21(5):217-220. [Abstract Only].
Sander et al., "Water jet guided Nd:YAG laser coagulation—its application in the field of gastroenterology," Endosc Surg Allied Technol. Aug. 1993; 1(4):233-238. [Abstract Only].
Stalder et al., "Repetitive Plasma Discharges in Saline Solutions," Appl. Phys. Lett. (Dec. 2001), 79(27):4503-4505.
Stoyanov, Daniel, "Surgical Vision", Annals of Biomedical Engineering (Oct. 20, 2011); 40(2): 332-345. Abstract Only.
Verdaasdonk et al., "Effect of microsecond pulse length and tip shape on explosive bubble formation of 2.78 μm Er,Cr;YSGG and 2.94 μm Er:YAG laser". Proceedings of SPIE, Jan. 23, 2012, vol. 8221-12, 1 page.
Woloszko et al., "Plasma Characteristics of Repetitively-Pulsed Electrical Discharges in Saline Solutions Used for Surgical Procedures," (2002) IEEE Trans. Plasma Sci. 30(3):1376-1383.
Wright, et al., "Cavitation of a submerged jet." Exp Fluids (2013); 54:1541, 21 pages.
Office Action (Non-Final) for U.S. Appl. No. 17/219,619, 33 sheets (May 11, 2023).
Feedback Loop Definition & Meaning, Your Dictionary, https://www.yourdictionary.com/feedback-loop, accessed Apr. 30, 2023 (Year: 2023).
Notice of Allowance dated Jun. 2, 2022 for U.S. Appl. No. 16/894,130, 13 pages.
Notice of Allowance for U.S. Appl. No. 16/846,159 dated Mar. 17, 2023, 8 pages.
Office Action for U.S. Appl. No. 17/955,233 dated Jan. 20, 2023, 7 pages.
Office Action for U.S. Appl. No. 16/846,159 dated Sep. 22, 2022, 11 pages.
Office Action for U.S. Appl. No. 17/125,586 dated May 4, 2023, 39 pages.
Office Action for U.S. Appl. No. 17/302,363 dated Dec. 8, 2022, 14 pages.
Office Action for U.S. Appl. No. 17/304,527 dated Mar. 7, 2023, 17 pages.
Sensor Definition & Meaning, Your Dictionary, https://www.yourdictionary.com/sensor, accessed Apr. 30, 2023 (Year: 2023).
Notice of Allowance for U.S. Appl. No. 16/846,159, 7 sheets, Jun. 28, 2023).
Notice of Allowance for U.S. Appl. No. 17/302,363, 8 sheets (Jun. 23, 2023).
Notice of Allowance for U.S. Appl. No. 17/304,527, 8 pages (Sep. 7, 2023).
Office Action for U.S. Appl. No. 17/643,963, 10 pages (Aug. 3, 2023).
Office Action for U.S. Appl. No. 17/955,233 dated Jul. 13, 2023, 37 pages.
Office Action (Non-Final) for U.S. Appl. No. 17/304,527, 9 pages (Dec. 12, 2023).
Office Action (Final) for U.S. Appl. No. 17/304,527, dated Apr. 19, 2024, 15 pages.
Office Action (Final) for U.S. Appl. No. 17/955,233, 30 sheets (Apr. 25, 2024).
Office Action (Final) for U.S. Appl. No. 17/955,233 dated Apr. 25, 2024, 28 pages.
Office Action (Final) for U.S. Appl. No. 17/643,963, dated Jul. 18, 2024 (10 pages).
Office Action (Non-Final) for U.S. Appl. No. 17/125,586, dated Jul. 18, 2024 (31 pages).
Office Action (Non-Final) for U.S. Appl. No. 18/345,078, dated Jun. 27, 2024 (17 pages).
Notice of Allowance for U.S. Appl. No. 17/304,527, dated Aug. 7, 2024 (13 pages).

\* cited by examiner

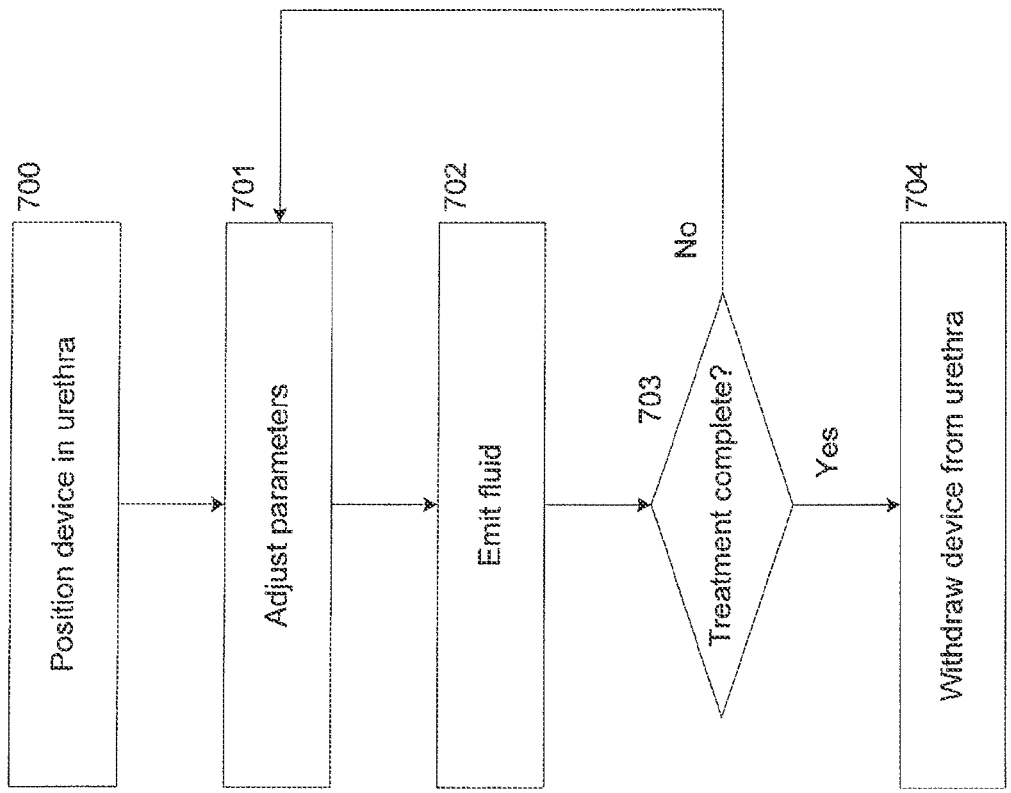

MINIMALLY INVASIVE TISSUE TREATMENT DEVICE

RELATED APPLICATIONS

This application is a divisional of U.S. patent application Ser. No. 16/392,984, filed Apr. 24, 2019, now U.S. Pat. No. 11,478,269, issued Oct. 25, 2022, which is a continuation of U.S. application Ser. No. 14/956,199, filed Dec. 1, 2015, now U.S. Pat. No. 10,321,931, issued Jun. 18, 2019, which is a continuation of U.S. patent application Ser. No. 13/790,218, filed Mar. 8, 2013, now U.S. Pat. No. 9,232,960, issued Jan. 12, 2016, which is a divisional of U.S. patent application Ser. No. 12/700,568, filed Feb. 4, 2010, now U.S. Pat. No. 9,232,959, issued Jan. 12, 2016, which is a continuation-in-part and claims priority to U.S. patent application Ser. No. 11/968,445, filed Jan. 2, 2008, now U.S. Pat. No. 7,882,841, issued Feb. 8, 2011, which non-provisional application claims the benefit of U.S. Provisional Patent Application No. 60/883,097, filed Jan. 2, 2007; U.S. application Ser. No. 12/700,568, filed Feb. 4, 2010, is a continuation-in-part application and claims priority to U.S. patent application Ser. No. 12/399,585, filed Mar. 6, 2009, now U.S. Pat. No. 8,814,921, issued Aug. 26, 2014, which non-provisional application claims priority to U.S. Provisional Patent Application No. 61/097,497, filed Sep. 16, 2008 and claims priority to U.S. Provisional Patent Application No. 61/034,412, filed Mar. 6, 2008, the full disclosures of which are incorporated herein by reference.

BACKGROUND

Field of Invention

The present invention relates generally to medical methods and devices. In particular, the present invention relates to methods and devices for applying energy to the urethra and the prostate to achieve volumetric tissue reduction.

A number of medical conditions affect the male urethra causing a variety of symptoms including painful or difficult urination, a swollen prostate, blood in the urine, lower back pain, and the like. Some of these conditions, such as prostatitis, are bacterial infections which can be treated with antibiotics and other drugs. Other conditions, however, such as benign prostatic hyperplasia (BPH) and prostatic carcinoma, result in enlargement of the prostate and obstruction of the urethra, sometimes leading to complete loss of bladder function.

Although various drug therapies for treating BPH have been proven to be effective, their effectiveness tends to be of limited duration, and often requires additional intervention such as surgical treatments.

Surgical treatment of BPH includes several variations of radical or partial prostatectomy involving complete or partial electrosurgical removal of the prostate. Prostatectomy constitutes the most invasive and effective treatment for the palliation of urinary flow obstruction secondary to constricting prostatic enlargement. It is still regarded by the American Urology Association (AUA) as the gold standard of care in the management of acutely symptomatic BPH, although its usage in urology practices has been rapidly declining due to the introduction of less invasive techniques. Open surgery-based radical prostatectomy is rarely employed in the treatment of BPH, being reserved almost exclusively for prostate cancer indications.

A prostatectomy may be achieved via open, laparoscopic, or transurethral approaches. The latter is preferred for a partial prostatectomy, which is typically performed in patients with acutely symptomatic BPH. Established versions of the technique include electrocautery-based transurethral resection of the prostate (TURP), transurethral vaporization of the prostate (TUVP), as well as transurethral incision of the prostate (TUIP), although the latter technique is used infrequently. In TURP, an electrosurgical loop is inserted into the urethra and used to remove excess prostatic tissue, whereas TUIP relies on cutting muscle adjacent to the prostate to relax the bladder opening to relieve difficulty in urination. TUVP was developed to produce comparable results to standard TURP while reducing procedural morbidity and hospitalization time. In TUVP, the electrosurgical loop is replaced with a roller ball capable of delivering sufficient energy to vaporize prostate tissue.

Over the last decade, medical device manufacturers have developed several minimally invasive (MI) directed energy-based techniques for BPH that are intended to reduce morbidity and complications with electrosurgical approaches, allow treatment in a more economical outpatient setting, and make it suitable for patients who fail drug therapy, but are not severe enough to warrant electrosurgical interventions such are TURP. Among these MI techniques are transurethral microwave thermotherapy (TUMT), RF-based transurethral needle ablation (TUNA), water-induced thermotherapy (WIT), as well as several laser ablation techniques using transurethral optical fibers such as interstitial laser coagulation of the prostate (ILC), holmium laser enucleation of the prostate (HoLEP), and photoselective vaporization of the prostate (PVP).

While generally successful, TUMP, TUNA, and WIT are inadequate to treat all patients and all conditions. In particular, patients having severe tissue intrusion into the urethral lumen resulting from BPH or prostatic cancer are difficult to treat with the above mentioned methods which rely on tissue shrinkage rather than resection. Thus, many of these patients will eventually require conventional surgical resection.

In contrast, HoLEP and PVP are capable of actively removing tissue by vaporization. However, HoLEP is limited by the long procedure time and the relatively high learning curve which has limited its dissemination.

Accordingly, the urological community has recently embraced the relatively technically less demanding PVP where a laser beam with output powers ranging from 60 to 120 W is directed from the urethra against prostatic tissue to achieve irradiance (power density) levels over a certain volumetric power density, referred to as a vaporization threshold, below which tissue coagulation rather than vaporization occurs. As the irradiance level increases above the vaporization threshold, tissue vaporization increases and coagulation decreases. However, the beam emitted from the probe in PVP systems is diverging. Therefore, the laser spot size enlarges with increasing probe distance from the tissue, and the power density decreases, reducing the rate of vaporization. Hence, in order to maximize the rate of tissue vaporization and thereby limit the extent of the zone of thermal damage characterized by tissue coagulation left after the procedure, the physician must steadily hold the fiber a fixed distance (e.g., 1-2 mm) away from the tissue and slowly scan the beam over the target tissue without varying the distance. As the procedure progresses, the tissue becomes carbonized and more difficult to ablate. Thus, a significant limitation of PVP is the decreasing rate of tissue removal as the procedure progresses, which dramatically increases procedure time, patient cost, and risk. Additionally, the effectiveness and duration of this procedure is highly dependent on the skill of the treating physician and the use of a very expensive high-power laser system.

Furthermore, most of the procedures described above require very high energies to coagulate and/or vaporize tissue, which can only be generated with large, high-power, and expensive equipment.

Additionally, current treatments of BPH are often associated with high risk of complications. For example, TURP is associated with retrograde ejaculation, post-operative irritation, erectile dysfunction, significant hematuria, and acute urinary retention and incontinence, among other complications. Post-treatment complications may be attributed to resecting, ablating, or otherwise damaging non-glandular tissues within the prostate-urethral region, such as the seminal vesicles, sphincter muscles, intra-prostate vessels, nervous tissues, or fibromuscular stroma. Additionally, treatment modalities that utilize selective thermolysis to ablate, coagulate, or denature targeted tissues to obtain sufficient reduction of prostate volume are likely to result in an extensive tissue zone of thermal damage. The consequences are the formation of edema and swelling of the heat-treated prostate tissue, often resulting in the inability to provide immediate symptomatic relief with the patient going into urinary retention and requiring post-procedure catheterization and hospitalization.

Furthermore, because the symptoms of prostatic disorders such as BPH often result in obstruction of the urethra, any trans-urethral prostatic treatment methods and devices are likely to be hindered by abnormal tissue occlusion. This is because the device may not be able to properly move within the occluded space to treat the desired area, thus preventing treatment devices from functioning properly or optimally. Additionally, abnormal tissue occlusion may also limit visualization of the treatment procedure and generally impedes optimal treatment.

For these reasons, it would be desirable to provide minimally invasive methods and devices which provide for enlarging the luminal area and/or volumetric resection of tissue surrounding the urethra. It would be particularly desirable if such methods and devices provided for heat-free removal of tissue, allowing tissue resection without inflicting thermal damage to tissue. It would be particularly desirable if such methods and devices provided for removal or destruction of such tissues surrounding the urethra where the removal or destruction products can be removed from the lumen to relieve pressure on the urethra, even when large volumes of tissue are being removed. Furthermore, it would be desirable for such methods and devices to minimize post-treatment complications by selectively resecting glandular tissue while leaving non-glandular tissue substantially undamaged. Additionally, it would be desirable for such methods and devices to expand the treatment region by creating a working space to enable better device movement and better visualization of the treatment region. Alternatively or additionally, the methods and devices should provide for anchoring of the treatment device relative to the urethra in order to provide a stable platform for treatment protocols. Methods and devices for performing such protocols should present minimal risk to the patient, should be relatively easy to perform by the treating physician, and should allow for alleviation of symptoms with minimal complications even in patients with severe disease. At least some of these objectives will be met by the inventions described below.

Description of the Background Art

Use of a transurethral endoscope for bipolar radiofrequency prostate vaporization is described in Boffo et al. (2001) J. Endourol. 15:313-316. Radiofrequency discharge in saline solutions to produce tissue-ablative plasmas is discussed in Woloszko et al. (2002) IEEE Trans. Plasma Sci. 30:1376-1383 and Stalder et al. (2001) Appl. Phys. Lett. 79:4503-4505. Air/water jets for resecting tissue are described in Jian and Jiajun (2001) Trans. ASME 246-248. US20050288639 described a needle injector on a catheter based system which can be anchored in a urethra by a balloon in the bladder. U.S. Pat. Nos. 6,890,332; 6,821,275; and 6,413,256 each describe catheters for producing an RF plasma for tissue ablation.

The use of lasers for cutting biological tissue is described in U.S. Patent Publication No. 20020128637 and for ablating prostate tissue is described in U.S. Pat. Nos. 5,257,991; 5,514,669; and 6,986,764. Pressurized water streams for effecting surgical incisions are described in U.S. Pat. Nos. 7,122,017; 5,620,414; and 5,505,729. The use of water or other fluid jets as waveguides for carrying a laser beam for cutting and other manufacturing operations is described in U.S. Patent Publication No. 20070278195, published Canadian application 2,330436 A1, PCT publication WO 99/56907, and U.S. Pat. Nos. 7,163,875; 5,902,499; and 5,773,791.

U.S. Pat. No. 6,960,182 describes using a liquid jet instrument to resect tissue such as the joint capsule of the knee, wherein a nozzle forms a liquid jet and the jet is received by a jet-receiving opening. U.S. Pat. No. 5,135,482 describes a hydrodynamic device for eliminating an organic deposit partially or completely obstructing a vessel of the human body. The patents do not disclose using a fluid stream to resect tissue within an enclosed tissue region such as the prostate-urethral region. U.S. Pat. No. 5,782,848 describes using a water jet to resect coagulated tissue. The patent does not disclose using a fluid stream to resect non-coagulated tissue or otherwise untreated tissue.

U.S. Pat. No. 5,207,672 describes compressing a portion of the prostate by using a balloon and ablating the tissue with a laser beam. The patent does not disclose expanding the urethra and then using a fluid stream to resect the tissue.

U.S. Pat. Nos. 4,560,373; 3,818,913; 4,913,698; 5,505,729; and U.S. Patent Publication Nos. 20090149712 and 20090157114 describe using a fluid stream to treat various tissues. The patents and patent applications do not describe using a fluid stream to resect tissue in an enclosed tissue region such as the prostate-urethral region. Various other aspects of fluid jet surgery apparatus such as pumps, applicators, and such are described in U.S. Pat. Nos. 5,037,431; 6,720,745; U.S. Patent Publication Nos. 20070129680, 20080038124, 20080243157, 20080221602, and 20090060764.

U.S. Patent Publication No. 20080097470 by Gruber et al. discloses the use of mechanical distension and fluid jet dissection in gynecological procedures. The application does not describe using a fluid stream to resect a volume of tissue. U.S. Patent Publication Nos. 20080188868, 20080249526, and 20090287045 disclose the use of fluid jet tissue resection, for example in laparoscopic procedures. As is commonly known, laparoscopic procedures create a working space in the abdominal cavity and the working space is not created inside the organ that is subject to surgery. The above mentioned publications do not describe inserting a device into an organ, creating a working space within the organ, and using a fluid stream to resect organ tissue.

SUMMARY

Methods, devices, and systems according to the present embodiments provide for the treatment of prostate tissue to relieve the symptoms of conditions such as BPH, prostatitis, and prostatic carcinoma, where enlargement of the prostate can obstruct the urethra and result in compression and partial or total occlusion of the urethra.

In a first aspect, a method for resecting prostate tissue comprises positioning a device having a fluid delivery element within a lumen of the urethra within the prostate. A fluid stream is directed outwardly from the fluid delivery element toward a wall of the urethral lumen. The fluid stream is sufficiently forceful to remove tissue. The fluid delivery element is moved to scan the fluid stream over the wall to remove a volume of tissue surrounding the lumen in order to relieve the symptoms associated with luminal blockage. The fluid delivery element may deliver water, saline, or other fluids, optionally combined with therapeutically active substances to combine the treatment with other therapies such as chemotherapy or the introduction of anesthetics, antibiotics, vaso-constricting and anti-inflammatory agents, or radiopharmaceuticals comprising therapeutic radioisotopes. The fluid may be combined with gases, soluble substances, or crystalline particles to increase resection efficiency.

The use of a fluid stream to resect tissue, according to the present embodiments, provides numerous advantages. Depending on selected configuration parameters such as fluid source pressures, fluid stream shapes, treatment times, and treatment patterns, the tissue resection proceeds very rapidly. The present fluid stream techniques resect tissue approximately an order of magnitude faster than traditional techniques such as laser ablation. Additionally, since heat sources are not needed for tissue resection, the present method is substantially heat-free, so does not leave a zone of thermal damage on the treated tissue. Hence, there will be little to no post-operative swelling, thereby eliminating or reducing the need for catheterization and yielding immediate relief from symptoms. Using a fluid stream to resect tissue also reduces patient risk by obviating the use of other energy sources inside the body which could otherwise lead to nerve damage.

The present fluid stream resection techniques also provide the advantage of selective tissue resection at appropriate pressures, wherein the fluid pressure and other characteristics can be configured such that soft tissue is removed while harder tissue, such as connective tissue, is largely unaffected by the fluid stream. Additionally, the fluid stream may be configured to be a diverging stream, thereby reducing the impact on tissue at greater distances from the fluid delivery element, which protects the prostate capsule and large arteries and veins from being damaged during surgery.

In order to gain a working space within the urethra, methods of the present invention may also comprise introducing a fluid to insufflate the urethra in the region of treatment before or while delivering a fluid stream to resect tissue. Such insufflation may be used to help control the distance from the pressurized fluid source to the tissue surface being treated. Furthermore, the insufflation fluid may be selected to be of a lower viscosity medium than the resection fluid, thereby lowering the resistance encountered by the resection fluid during tissue resection and maintaining integrity of the resection fluid stream shape. Additionally, the two fluids may be chosen such that a difference in their refractive indices provides for internal reflection, and in particular total internal reflection, within the resection fluid and allows the resection fluid to serve as a conduit for electromagnetic energy transmission, for example for cauterization or other energy delivery to tissue. Optionally, a working space may be created using mechanical means.

The methods of the present invention may further comprise removing fluid which has been delivered to the treatment area as well as tissue debris and fluid produced by resection. The treatment area may further be flushed or injected with saline or other fluid prior to, during, or after treatment with the fluid stream.

While tissue resection according to the present embodiments will typically be effected using a forceful fluid stream, in some instances it may be beneficial to provide for the delivery of other treatment energies before, during, or after the delivery of the forceful fluid stream. In such other methods, the fluid stream may not be sufficiently forceful to resect tissue. Such energy may be delivered to enhance tissue resection, but will often be delivered to provide for cauterization of the tissue, typically delivered after completion of the treatment with the forceful fluid stream. Suitable energy sources include laser energy, radiofrequency energy, heat, cold, and the like, and may broadly include applying any electromagnetic, mechanical, vibrational, thermal, and/or electrical energy.

Positioning of the pressurized fluid source will typically comprise advancing a probe into the urethra, directing the pressurized fluid through a fluid delivery element (such as a nozzle or plurality of nozzles) which is movably mounted on the probe, and moving the fluid delivery element relative to the probe to scan the fluid stream over the wall. The probe may be anchored by a balloon or other expandable element on a distal end of the probe, and/or by an external anchoring frame configured to atraumatically engage an external body surface area such as the base of the penis, thereby stabilizing the probe against proximal and distal dislodgement. By thus anchoring a distal end of the probe in the bladder, the position of the fluid delivery element on the probe will be precisely defined relative to the bladder neck, thus facilitating positioning the fluid delivery element precisely at the prostatic tissue within the urethra. The use of the anchor is particularly advantageous since it allows the present procedures to be performed without endoscopic, fluoroscopic, or other imaging, although the present procedures may also be performed in combination with imaging techniques. The device stability provided by the anchor also allows precision movement of the fluid delivery element which in turn aids in automation of the procedure.

The fluid delivery element will typically be positioned at the end of a lumen or tube which passes through or over the probe and allows for translation and/or rotation of the fluid delivery element relative to an axis of the probe. The fluid stream may diverge, converge, or remain with a constant cross-sectional area after it exits the fluid delivery element. Typically, the fluid delivery element will be moved in a pre-defined manner to cover and treat a cylindrical volume of prostatic tissue surrounding the urethra. Alternatively, the fluid delivery element may be scanned to cover a non-cylindrical and optionally non-symmetric region within the urethra which has been targeted for treatment. Typically, the pressurized fluid source will include a powered pump which can be controllably driven to deliver the desired pressure through the fluid delivery element.

The present invention further provides devices for treating prostate. Such devices comprise an elongate element (e.g., a shaft) having a proximal end and a distal end. An expandable anchor, such as an inflatable balloon, is secured at or near the distal end of the elongate element for anchoring the element in the bladder, and an external anchoring frame may provide additional stability by engaging an external body surface, such as the base of the penis. At least one fluid delivery element is coupled to the elongate element and disposed proximally to the anchor. The fluid delivery element may be moved relative to the elongate element, typically being movable in an axial, rotational, or oscillatory motion relative to the elongate element. Fluid may be directed at a generally perpendicular or normal angle relative to the elongate element, and may also be directed at other angles relative to the elongate element. The elongate element may comprise one or more lumens for performing additional portions of the protocols of the present invention. For example, a lumen may be provided for delivering pressurized gas or other fluids to the urethra for insufflating the urethra. Further lumens may be provided for removing resection debris from the treatment area, for delivering flushing fluid, and the like. The elongate element will have dimensions suitable for introduction through the urethra to the prostate. The elongate element may comprise means for delivering any of the energy sources discussed herein with respect to the method, including laser energy, radiofrequency energy, heat, cold, and the like.

While the present invention is specifically directed at transurethral treatment of the prostate, certain aspects of the invention may also be used to treat and modify other organs such as brain, heart, lungs, intestines, eyes, skin, kidney, liver, pancreas, stomach, uterus, ovaries, testicles, bladder, ear, nose, etc., soft tissues such as bone marrow, adipose tissue, muscle, glandular tissue, spinal tissue, etc., hard biological tissues such as teeth, bone, etc. as well as body lumens and passages such as the sinuses, ureter, colon, esophagus, lung passages, blood vessels, etc. The devices disclosed herein may be inserted through an existing body lumen, or inserted through solid body tissue.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 9a is a flow diagram illustrating selective and controlled resection.

DETAILED DESCRIPTION

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as described here.

Figure 1:
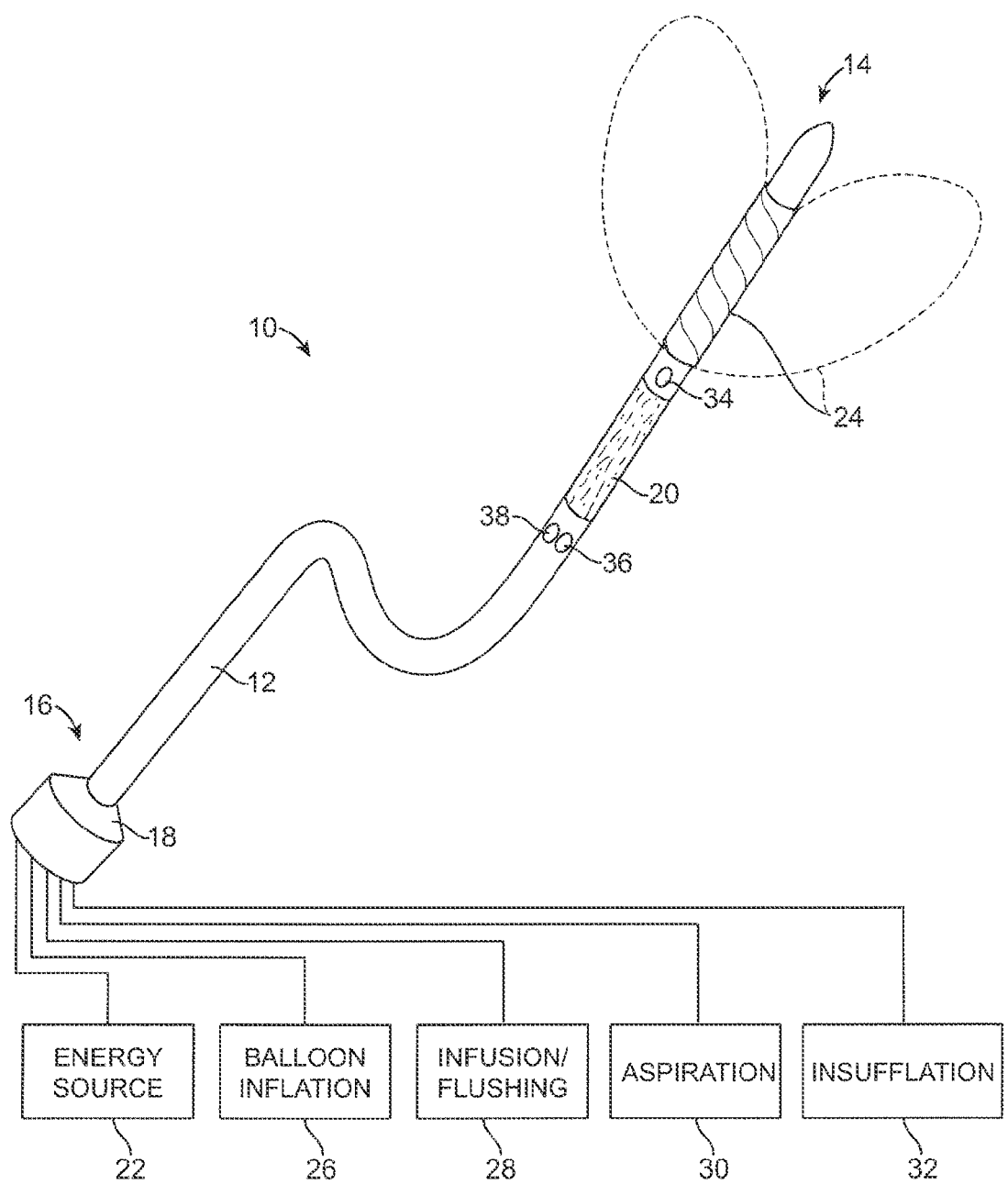
FIG. 1 is a schematic illustration of a device suitable for performing intraurethral prostatic tissue debulking in accordance with the principles of the present invention.

Referring to FIG. 1, an exemplary prostatic tissue debulking device 10 constructed in accordance with the principles of the present invention comprises a catheter assembly generally including a shaft 12 having a distal end 14 and a proximal end 16. The shaft 12 will typically be a polymeric extrusion including one, two, three, four, or more axial lumens extending from a hub 18 at the proximal end 16 to locations near the distal end 14. The shaft 12 will generally have a length in the range from 15 cm to 25 cm and a diameter in the range from 1 mm to 10 mm, usually from 2 mm to 6 mm. The shaft will have sufficient column strength so that it may be introduced upwardly through the male urethra, as described in more detail below.

The shaft will include an energy source positioned in the energy delivery region 20, where the energy source can be any one of a number of specific components as discussed in more detail below. Distal to the energy delivery region, an inflatable anchoring balloon 24 will be positioned at or very close to the distal end 14 of the shaft. The balloon will be connected through one of the axial lumens to a balloon inflation source 26 connected through the hub 18. In addition to the energy source 22 and the balloon inflation source 26, the hub will optionally further include connections for an infusion/flushing source 28, an aspiration (a vacuum) source 30, and/or an insufflation (pressurized $CO_2$ or other gas) source 32. In the exemplary embodiment, the infusion or flushing source 28 can be connected through an axial lumen (not shown) to one or more delivery ports 34 proximal to the balloon anchor 24 and distal to the energy delivery region 20. The aspiration source 30 can be connected to a second port or opening 36, usually positioned proximally of the energy delivery region 20, while the insufflation source 32 can be connected to an additional port 38, also usually located proximal of the energy delivery region. It will be appreciated that the locations of the ports 34, 36, and 38 are not critical, although certain positions may result in particular advantages described herein, and that the lumens and delivery means could be provided by additional catheters, tubes, and the like, for example including coaxial sleeves, sheaths, and the like which could be positioned over the shaft 12.

Figure 2A:
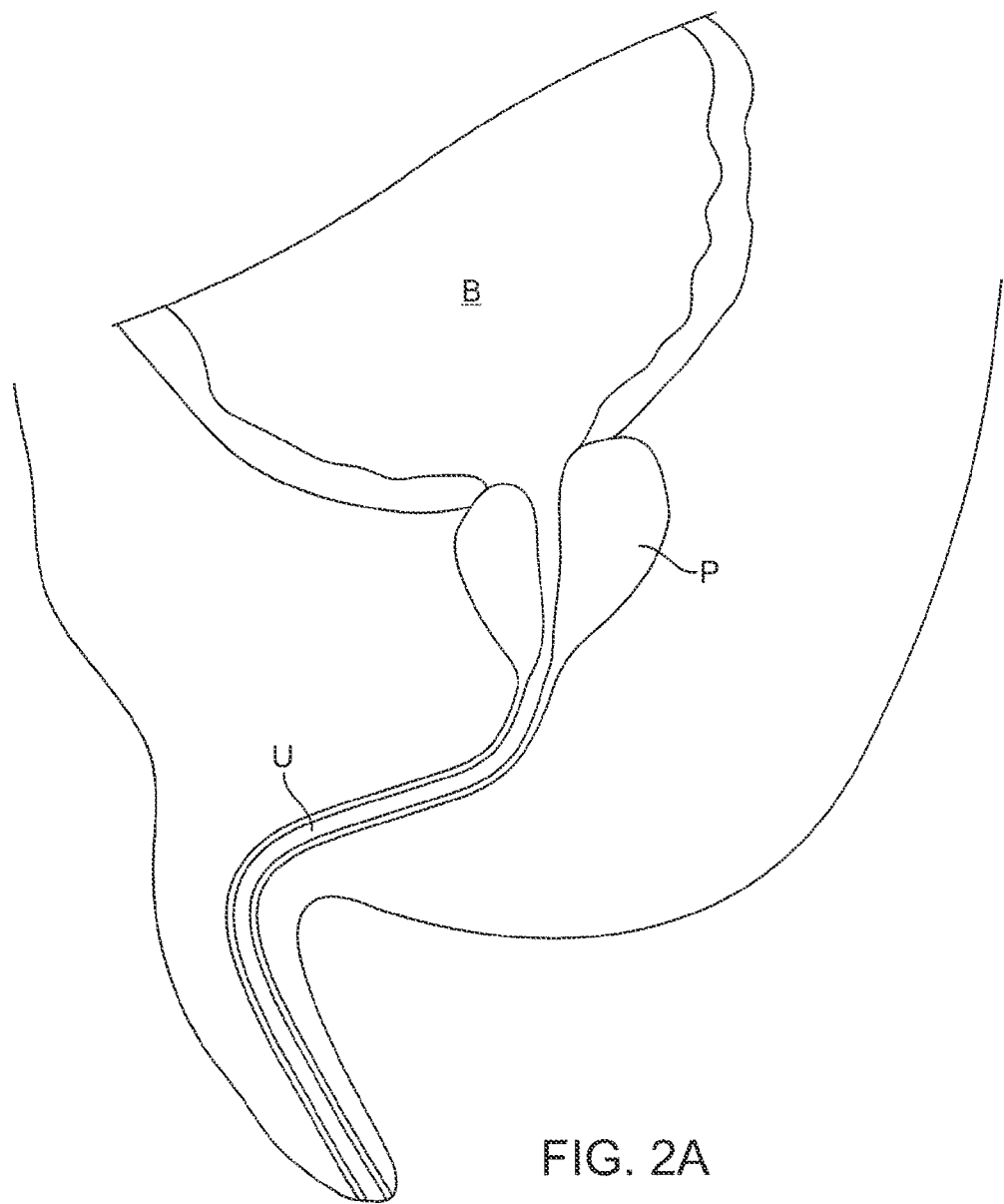
FIGS. 2A-2D illustrate use of the device of FIG. 1 in performing prostatic tissue debulking.
Figure 2B:
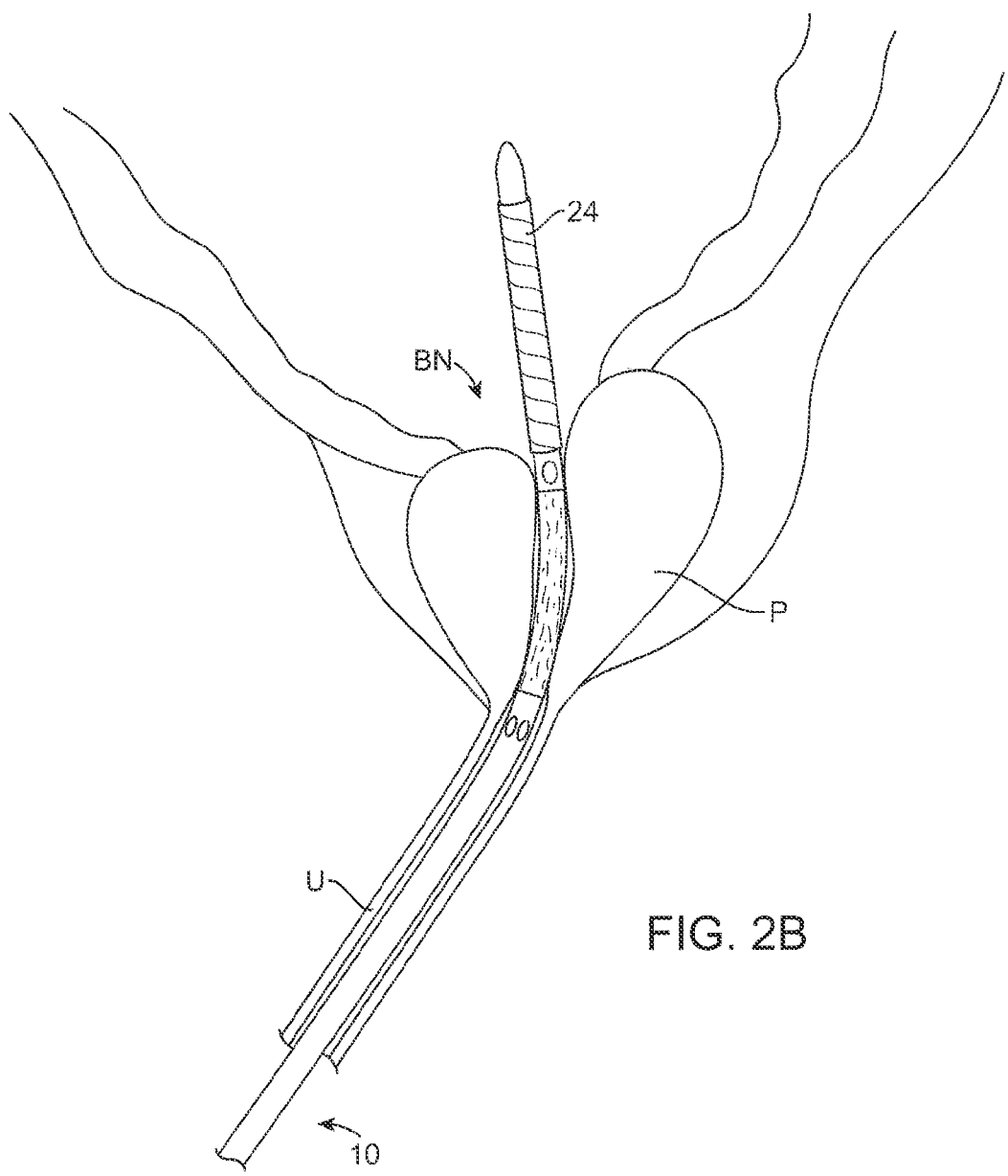
Figure 2C:
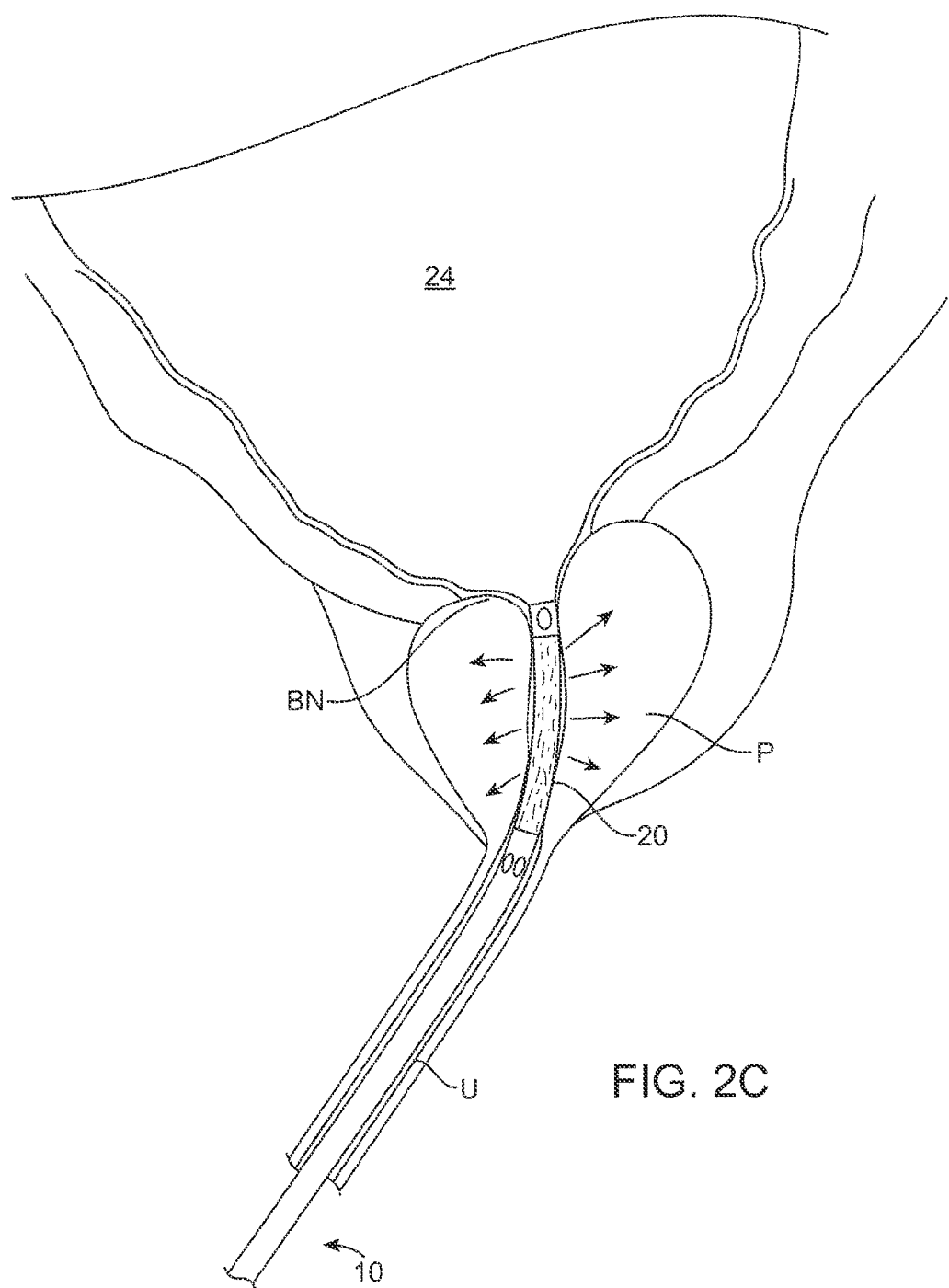
Figure 2D:
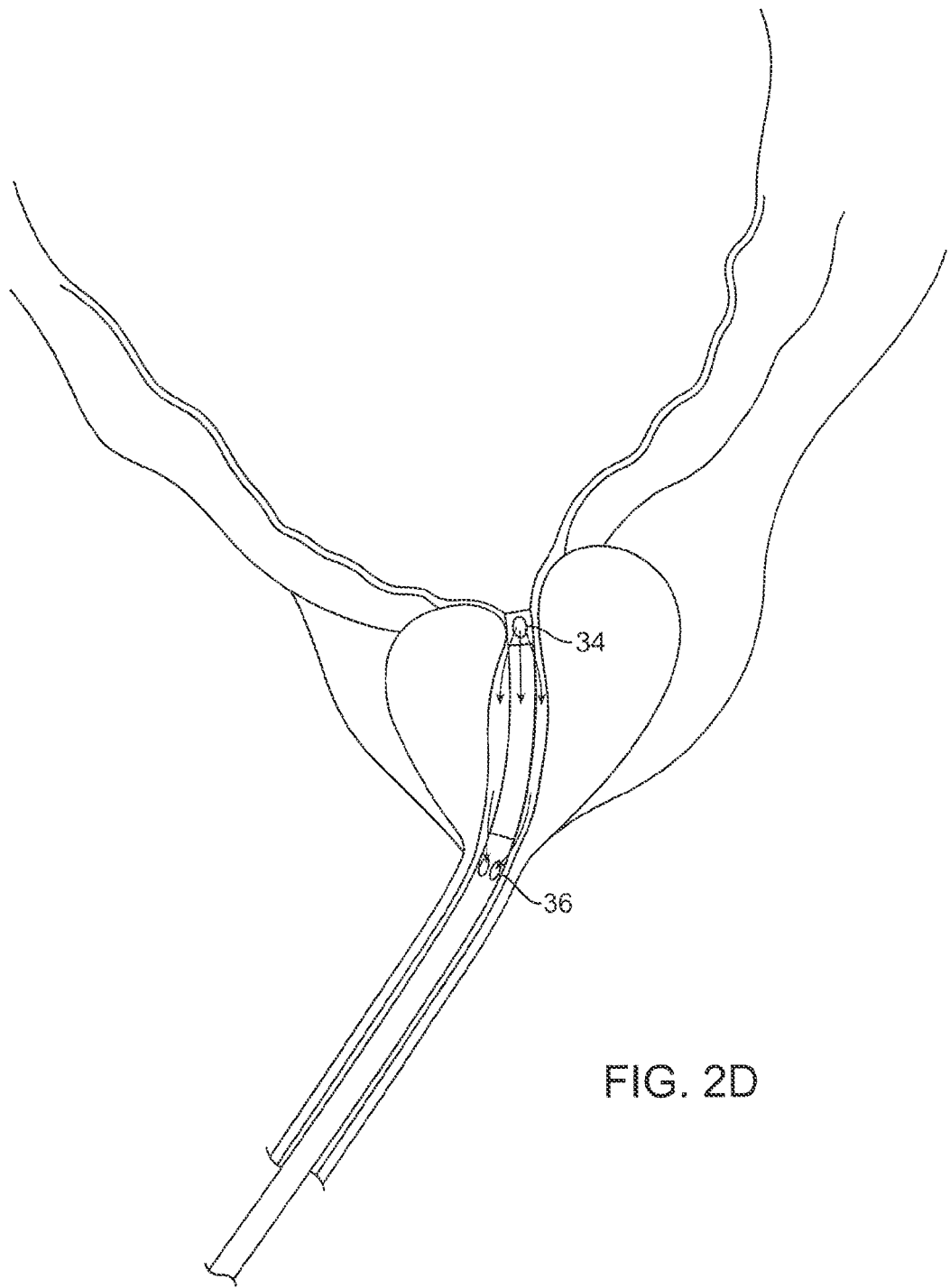

While the present embodiments are described with reference to the human prostate, it is understood that they may be used to treat mammal prostates in general. Referring now to FIGS. 2A-2D, the prostatic tissue debulking device 10 is introduced through the male urethra U to a region within the prostate P which is located immediately distal to the bladder B. The anatomy is shown in FIG. 2A. Once the catheter 10 has been positioned so that the anchoring balloon 24 is located just distal of the bladder neck BN (FIG. 2B) the balloon can be inflated, preferably to occupy substantially the entire interior of the bladder, as shown in FIG. 2C. Once the anchoring balloon 24 is inflated, the position of the prostatic tissue debulking device 10 will be fixed and stabilized within the urethra U so that the energy delivery region 20 is positioned within the prostate P. It will be appreciated that proper positioning of the energy delivery region 20 depends only on the inflation of the anchoring balloon 24 within the bladder. As the prostate is located immediately proximal to the bladder neck BN, by spacing the distal end of the energy delivery region very close to the proximal end of the balloon, typically within the range from 0 mm to 5 mm, preferably from 1 mm to 3 mm, the delivery region can be properly located. After the anchoring balloon 24 has been inflated, energy can be delivered into the prostate for debulking, as shown by the arrows in FIG. 2. Once the energy has been delivered for a time and over a desired surface region, the energy region can be stopped and the prostate will be debulked to relieve pressure on the urethra, as shown in FIG. 2D. At that time, a flushing fluid may be delivered through port 34 and aspirated into port 36, as shown in FIG. 2D. Optionally, after the treatment, the area could be cauterized using a cauterizing balloon and/or stent which could be placed using a modified or separate catheter device.

Figure 3:
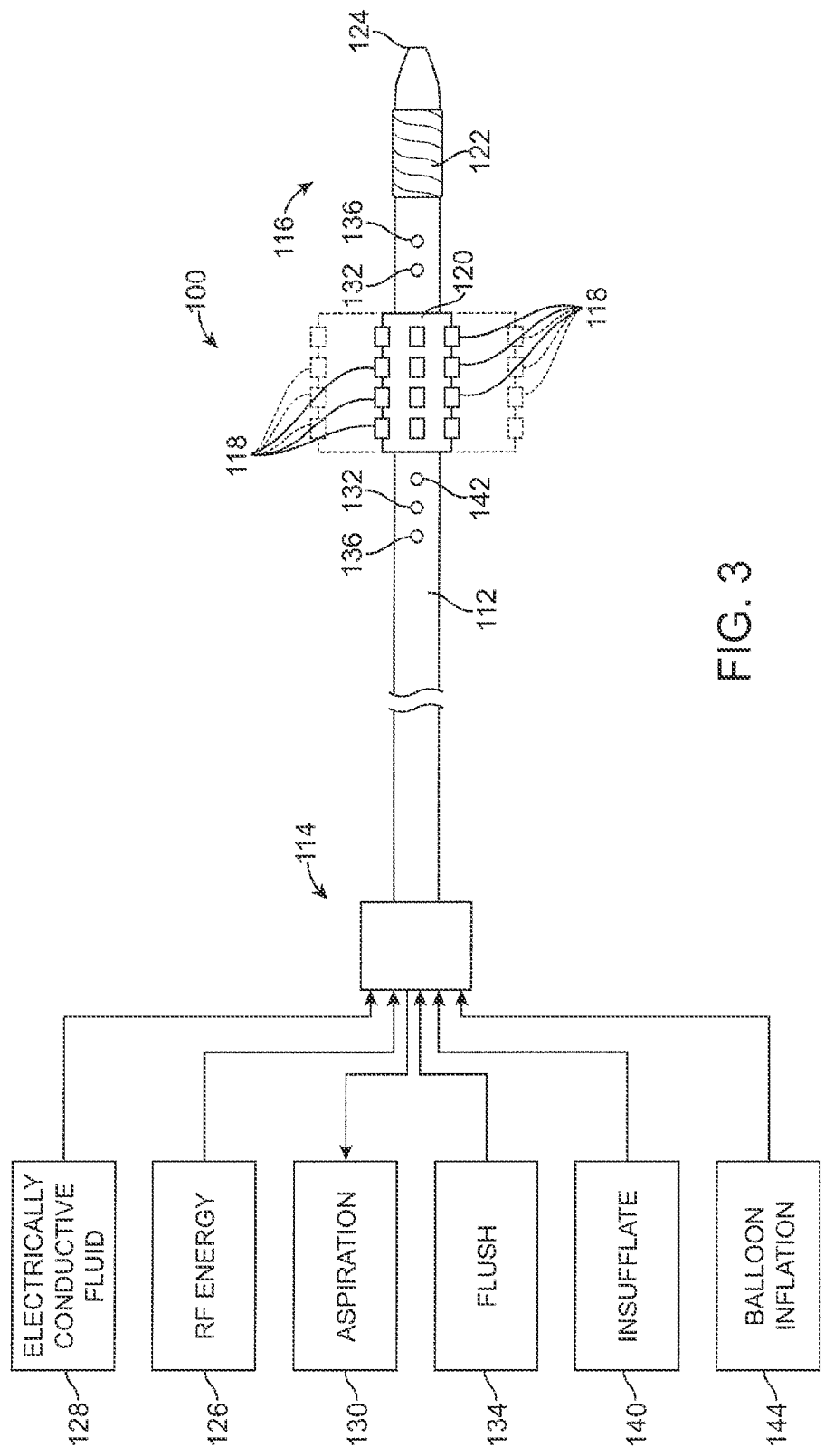
FIG. 3 illustrates a specific prostatic tissue treatment device incorporating the use of a radiofrequency saline plasma for performing prostatic tissue debulking.

Referring now to FIGS. 3-7, a number of representative energy delivery regions will be described. Referring now to FIG. 3, a first exemplary prostate resection device 110 constructed in accordance with the principles of the present invention comprises a shaft 112 having a proximal end 114 and a distal end 116. A plurality of nozzles 118 are mounted on the shaft 112 at a location spaced proximally from the distal end 116 by distance in the range from 1 cm to 5 cm. The nozzles, which are typically ceramic cores capable of generating a plasma or ports capable of directing a radially outward stream of electrically conductive fluid, may be mounted on structure 120, which allows the nozzles 118 to be moved radially outwardly, as shown in broken line in FIG. 3. An anchor 122, shown as an inflatable balloon is mounted on the distal end 116 of the shaft 112 at a location between the nozzles 118 and the distal tip 124. The expandable structure 122 will be capable of being expanded within the bladder to anchor the shaft 112 so that the nozzle array 118 lies within the prostate, as described in more detail below. The shaft 112 will include lumens, passages, electrically conductive wires, and the like, in order to deliver energy and materials from the proximal end 114 to the distal end 116 of the shaft. For example, an RF energy source 126 will be connected to the shaft 112, usually to the nozzles 118, in order to deliver RF energy to an electrically conductive fluid delivered from source 128 to the nozzles 118, typically through a lumen within the shaft 112. Other lumens, channels, or conduits will be provided in order to allow aspiration to a vacuum source 130 which is typically connected to one or more aspiration ports 132. Other conduits may be provided within the shaft 112 in order to permit introduction of a flushing fluid, such as saline, from a source 134 to ports 136. In other instances, it will be possible to connect the aspiration and flushing sources 130 and 134 to a common port so that aspiration and flushing may be conducted sequentially rather than simultaneously. Further optionally, internal lumens, conduits, or the like, may be provided in order to connect a source of insufflation 140 to one or more insufflation ports 142 on the shaft in the region of the array 118. Finally, internal lumens, conduits, or the like, may be provided for connecting balloon 122 to a balloon inflation source 144.

Figure 4:
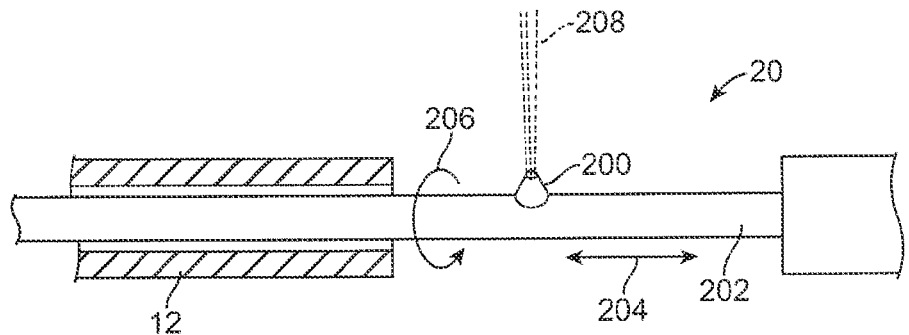
FIG. 4 illustrates an energy source suitable for use in the devices of the present invention, wherein the energy source delivers a fluid stream for tissue resection.

As shown in FIG. 4, an exemplary energy delivery region 20 can be formed by a high pressure nozzle 200 which is carried on a delivery tube 380 which is disposed within the shaft 12. Carrier tube 202 may be axially translated as shown by arrow 204 and/or rotated as shown by arrow 206 so that the fluid stream 208 emanating from the nozzle 200 can be scanned or rastered over all or a selected portion of the urethra within the prostate. Specific pressures and other details for such high pressure water treatment are described, for example, in Jian and Jiajun, supra.

Figure 5:
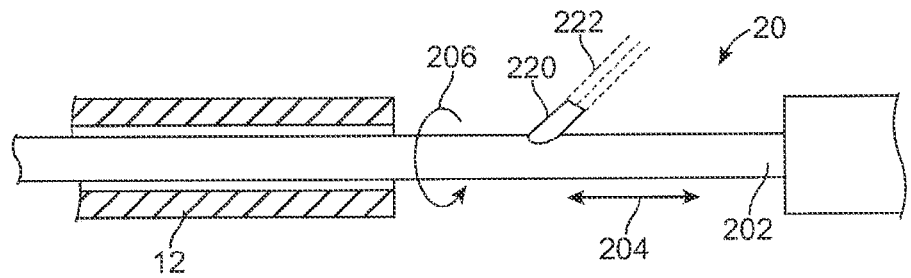
FIG. 5 illustrates an energy source suitable for use in devices of the present invention, wherein the energy source comprises a deflected optical waveguide for delivering laser energy to the prostatic tissue.

Referring now to FIG. 5, the energy source within the energy delivery region 20 may comprise a fiber-optic waveguide or fiber bundle 220 carried on the rotating and translating shaft 380. The optical waveguide 220 transmits laser or other coherent optical energy in a beam 222 which may be scanned or rastered over the urethral wall and prostatic tissue by rotating and/or translating the carrier tube 202.

Figure 6:
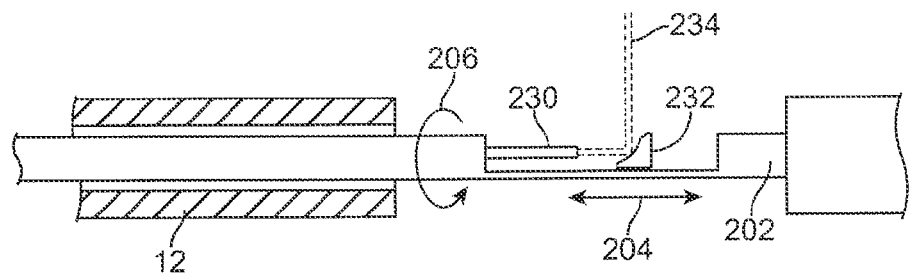
FIG. 6 illustrates a device similar to that shown in FIG. 5, except the optical waveguide directs laser energy at a mirror which laterally deflects the laser energy.

As shown in FIG. 6, laser energy from an optical waveguide or fiber bundle 230 may be directed axially against a mirror 232, where the waveguide and mirror are both carried on the rotating and axially translating carrier tube 202. Again, by rotating and/or translating the carrier tube 202, the emanating beam 234 can be scanned or rastered over the urethral wall.

Figure 7:
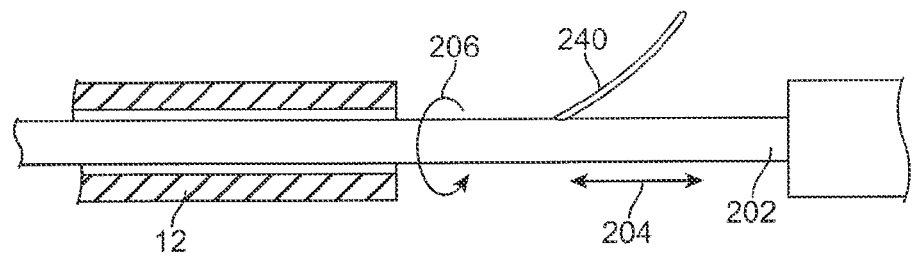
FIG. 7 illustrates an energy source suitable for use in the devices of the present invention, wherein the energy source comprises a laterally projecting electrode which can engage the urethral wall and prostatic tissue to deliver radiofrequency energy for tissue ablation.

Referring now to FIG. 7, in yet another embodiment, the rotating and axially translating tube 202 may carry an electrode 240 which projects laterally from the tube. The electrode 240 will be adapted for connection to a radiofrequency energy source so that, when the electrode contacts the urethral wall and prostatic tissue, radiofrequency energy can be delivered, either in a monopolar or bipolar mode. The radiofrequency energy can thus ablate the tissue over selected volumes and regions of the prostatic tissue. Optionally, by changing the nature of the radiofrequency energy, the electrode 240 could also be used to cauterize the tissue after it has been treated.

In one embodiment of the present invention, the device is configured to selectively resect tissue, causing the removal of some tissue compositions while leaving other tissue compositions intact. For example, the prostate and nearby regions comprise a variety of tissue compositions, including glandular prostate tissue, intra-prostate vessels, fibromuscular stroma, capsular tissue, sphincter muscles, seminal vesicles, etc. When treating BPH or other prostate conditions, it is desirable to remove glandular prostate tissue and leave other tissues, such as vessels and capsular tissue, substantially undamaged.

As referred to herein, the term resection is meant to include any removal of tissue, including removal of one or more conglomerates of tissue cells, removal of fractions of tissue cells, etc.

One advantage of treating BPH by selective tissue resection is the reduced need (or no need) for cauterization, since there is little or no damage to intra-prostate blood vessels and as a result there is limited bleeding. Another advantage is a decreased chance of incontinence or impotence, since selective resection decreases the risk of perforating or otherwise damaging surrounding tissues, such as the prostate capsule, sphincter muscles, seminal vesicles, etc.

When using a fluid stream to resect tissue, selective tissue resection may be accomplished by varying one or more parameters of the fluid stream, such as the pressure within a nozzle or other fluid delivery element, or the flow rate of the fluid in the stream, so that it resects some tissue compositions while leaving other tissue compositions substantially undamaged.

In one embodiment, the fluid stream parameters may be configured to leave non-target tissues substantially undamaged even when those tissues are exposed to the fluid stream for an extended period of time, i.e., typically a period of time that is sufficient to achieve the desired resection. In another embodiment, the fluid stream parameters may be configured to resect the target tissue at a substantially higher rate than the non-target tissue, thereby limiting damage to non-target tissue. Such parameters may be adjusted, depending on the target tissue that is to be selectively resected.

In one embodiment, the rate of resection is configured to be higher for glandular tissue than for non-glandular tissue. The rate of resection may be configured by altering the pressure of the fluid, or by adjusting other fluid parameters, as described above. In particular, the rate of resection for glandular tissue may be configured to be significantly higher than that for non-glandular tissue, such that during the treatment period non-glandular tissue remains effectively undamaged. For example, the rate of resection of glandular tissue may be configured to be at least twice as high as that for non-glandular tissue. As another example, the rate of resection for glandular tissue may be configured to be at least 10 times as high as that for non-glandular tissue.

It is noted that tissue resection has a critical pressure (which is a pressure below which tissue does not resect and above which tissue can be resected) because the removal process involves tearing of the tissue, wherein tissue is stretched on a micro scale to the point where the tissue matrix ruptures or tears. Since tissue is elastic, there will be a critical breaking point. Different types of tissue will have different critical breaking points, and hence different critical pressures associated with them.

Indeed, given a particular fluid delivery element size (such as nozzle diameter), each tissue type typically has a critical pressure of the fluid stream source (hereinafter also referred to as $P_{crit}$) below which the rate of resection approaches zero, and above which the rate of resection generally increases monotonically, and possibly exponentially. Specifically, due to differences in tissue composition, the pressure of the fluid stream source may be configured to selectively resect a particular type of tissue while leaving other tissue types with higher critical pressures generally undamaged.

Figure 8:
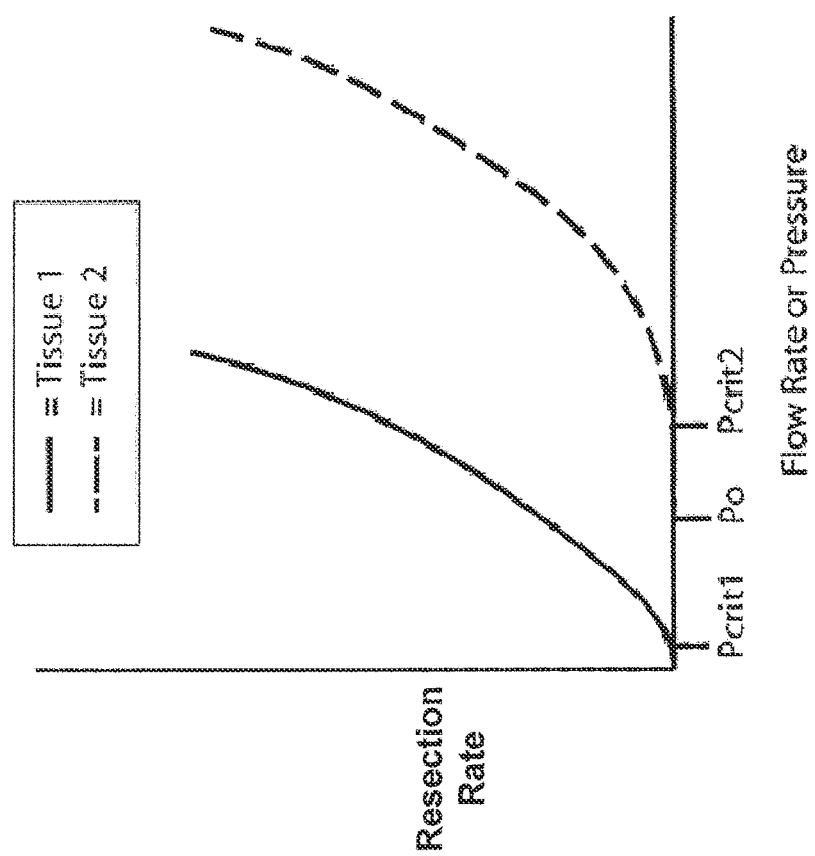
FIG. 8 is a graph of tissue resection rates demonstrating critical pressures.

An important aspect of resecting tissue in a multi-tissue environment according to the present embodiments is that it is possible to operate in a regime where one tissue type is resected and another tissue type remains substantially undamaged. This happens most strongly when operating at a pressure between the critical pressures of the two tissue types. As seen in FIG. 8, the operating pressure $P_o$ of the fluid stream may be configured to be greater than the critical pressure of tissue 1 ($P_o > P_{crit1}$) so that tissue 1 experiences a resection rate that is greater than zero, while keeping the pressure $P_o$ less than the critical pressure of tissue 2 ($P_o < P_{crit2}$) so that tissue 2 experiences a rate of resection that is substantially near zero. In such a configuration, the fluid stream is said to be configured to selectively resect tissue 1 but not tissue 2.

In one embodiment configured to treat BPH, the fluid stream source pressure is configured to be above the critical pressure of glandular prostate tissue but below the critical pressure of non-glandular prostate tissue. In such an embodiment, the pressure is sufficiently high to resect glandular tissue, but too low to substantially resect or damage non-glandular tissue such as intra-prostate blood vessels, fibromuscular stroma, capsular tissue, etc. In one embodiment, the fluid is pressurized to a pressure within the range of about 1-30,000 psi before leaving the fluid delivery element, more preferably to a pressure within the range of about 50-1,500 psi, and most preferably to a pressure within the range of about 100-1,000 psi.

The following example illustrates some tissue critical pressures for fluid stream resection. It is noted that the following configurations are provided as an example and should not be construed as limiting.

EXAMPLE 1: Exemplary Critical Pressures of Different Kidney Tissue Compositions

Tissue critical pressures were measured in pig kidneys. Kidney tissue was chosen because its composition is similar to that of the prostate tissue. A columnar fluid stream of approximately 200 microns in diameter was used for tissue resection. The glandular tissue (the pink outer portion of the kidney) is very soft, and easily tears with finger pressure, while the inside of the kidney comprises tougher vascular tissue. The critical pressure for the glandular tissue with this fluid stream was found to be about 80 psi, and about 500 psi for the vascular tissue, as seen in Table 1 below.

TABLE 1

Different critical pressures of glandular and vascular tissues in pig kidney

| Tissue | $P_{crit}$ (psi) |
| --- | --- |
| Glandular | 80 |
| Vascular | 500 |

For example, experiments show that when resecting pig kidney using a nozzle of approximately 200 microns in diameter with liquid source pressure of about 500 psi, the rate of resection over a 10 cm² area is about 1 cm per 30 sec for glandular tissue (i.e., removal of 10 cc per 30 sec), and less than about 0.1 cm per 180 sec for vascular tissue, which is about a sixty-fold difference in resection rates. Thus, within the same resection time period, more glandular tissue will be resected than vascular tissue. Thereby, the resection time period can be configured to allow resection of glandular tissue without substantial damage to vascular tissue. The rate of resection may be adjusted by varying the fluid source pressure and/or the size of the nozzle. For example, the rate of resection for glandular tissue may be adjusted to about 1 cc per min, 5 cc per min, 10 cc per min, 30 cc per min, or other rates. As noted above, it is understood herein that varying the size of the nozzle may necessitate varying the fluid source pressure in order to cause the fluid stream to impinge with sufficient force upon tissue to achieve desired resection rates.

FIG. 9a is a flow diagram illustrating a method for selective prostate resection, according to one embodiment. At step 700, the device is positioned and anchored in the urethra, as described above. At step 701, various fluid parameters such as the pressure of the fluid source, shape of the fluid stream, etc., are configured to resect a specific tissue type, such as glandular prostate tissue. By configuring the fluid parameters one can control fluid force, rate of resection, treatment time, area of tissue to be resected, etc., in order to achieve controlled and selective resection. After the parameters are configured, at step 702, the device is configured to discharge a fluid stream to resect the target tissue. At step 703, if it is determined that the treatment is complete, the device is withdrawn from the urethra U at step 704.

However, if at step 703 it is determined that the treatment is not yet complete, then the fluid parameters may be re-configured as needed, as described in step 701, and the cycle of steps repeats until treatment is complete. In particular, re-configuration of the fluid parameters is advantageous in an embodiment where it is desired to resect two different types of tissues for a complete treatment. In such an embodiment, the fluid parameters may be adjusted to take into account the change in the type of target tissue that is to be resected.

Typically, after some or all of the glandular tissue has been resected, other tissue types such as vascular or capsular tissue will be exposed to the fluid stream. While the fluid stream parameters are configured to selectively resect glandular tissue, it is also contemplated that the fluid parameters may be dynamically adjusted during the resection procedure to take into account the gradual exposure of non-glandular tissue and to fine-tune the resection selectivity as needed. After the fluid parameters are thusly re-configured at step 701, then at step 702 the re-configured fluid stream is emitted to continue tissue resection, and the operation continues until the treatment is complete.

Specifically, it is noted that when treating the prostate from within the urethra, the urethral wall is interposed between the source of the fluid stream (such as a nozzle or other fluid delivery element) and the target glandular prostate tissue that is to be resected. Therefore, in one embodiment, the fluid stream parameters are initially configured to resect and penetrate a portion of urethral tissue (e.g., the urethral wall). However, since the composition of glandular prostate tissue is weaker than that of the urethral tissue, it is desirable to avoid resecting glandular tissue with the same fluid stream force as that used to resect the urethral wall. To accomplish this, the fluid stream may be used for a period of time that is sufficient to resect and penetrate the urethral wall, and not longer. Thereafter, a fluid stream of reduced strength may be used to resect glandular prostate tissue.

Figure 9B:
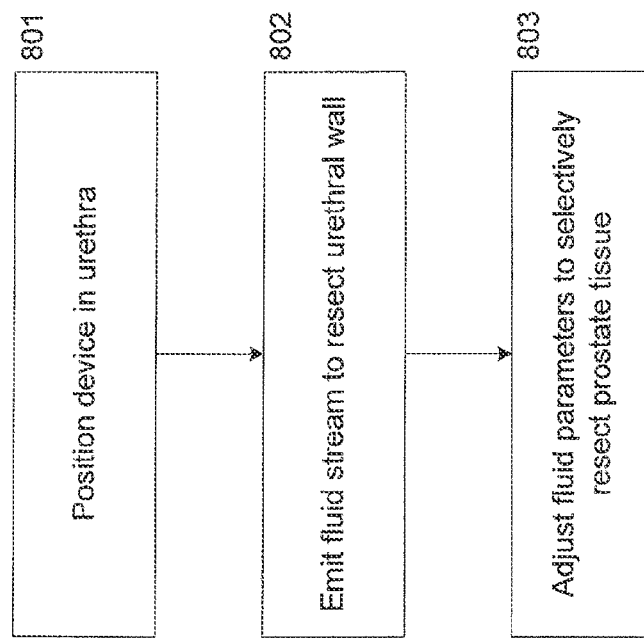
FIG. 9b is a flow diagram illustrating selective resection, wherein the fluid stream is configured to penetrate the urethral wall before resecting the prostate tissue.

FIG. 9b is a flow diagram illustrating a method for selective prostate resection, wherein the fluid stream is configured to first penetrate and resect the urethral wall, according to one embodiment. At step 801, the device is positioned and anchored in the urethra, as described above. At step 802, the device is configured to discharge a fluid stream of sufficient force to resect and penetrate the urethral wall. At step 803, after the fluid stream has penetrated the urethral wall, the fluid stream is adjusted to a level that selectively resects the desired prostate tissue while leaving intra-prostate blood vessels, capsules, and other non-glandular tissue substantially undamaged.

In addition, it is contemplated that the shape of the fluid stream also affects selective resection. While the fluid stream is exemplarily shown in FIG. 10a as a columnar fluid stream 333 or diverging fluid stream 334, it is contemplated that the fluid stream may be of any shape or configuration that allows resection according to the present embodiments. In particular, there are numerous advantages to both the columnar fluid stream configuration and the diverging fluid stream configuration, as will be described further below.

In a columnar fluid stream configuration 333, the device emits the fluid stream as a substantially focused rod-like fluid column that has a substantially zero divergence angle. In one embodiment, the columnar fluid stream is configured as a generally straight or non-diverging fluid stream. In such configuration, the device emits the fluid stream substantially as a cylinder or other non-diverging shape, thereby transmitting energy to the tissue over an area or spot size that is largely independent of the tissue distance from the fluid delivery element. Optionally, the fluid stream may be adjusted to converge, for example if the fluid delivery element comprises multiple nozzles or if the fluid contains bubbles, in order to focus the energy delivered to tissue.

Figure 10A:
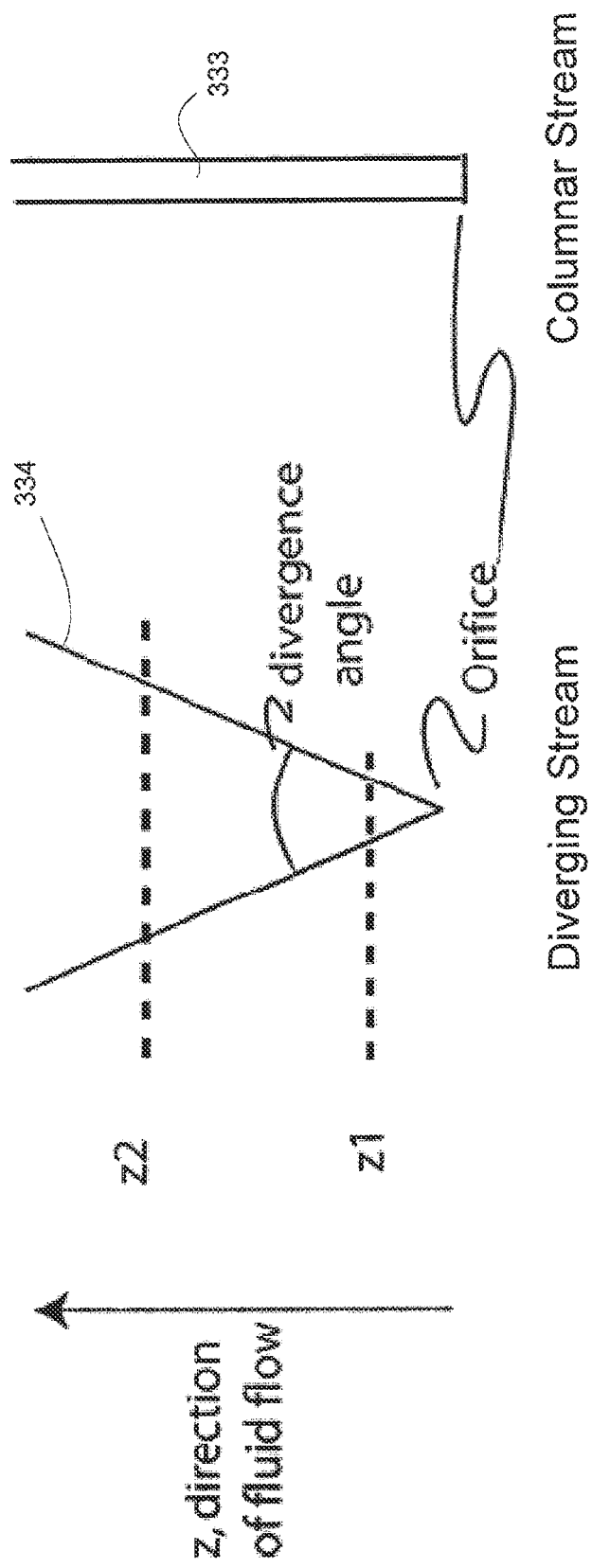
FIG. 10a illustrates a columnar fluid stream and a diverging fluid stream.
Figure 10B:
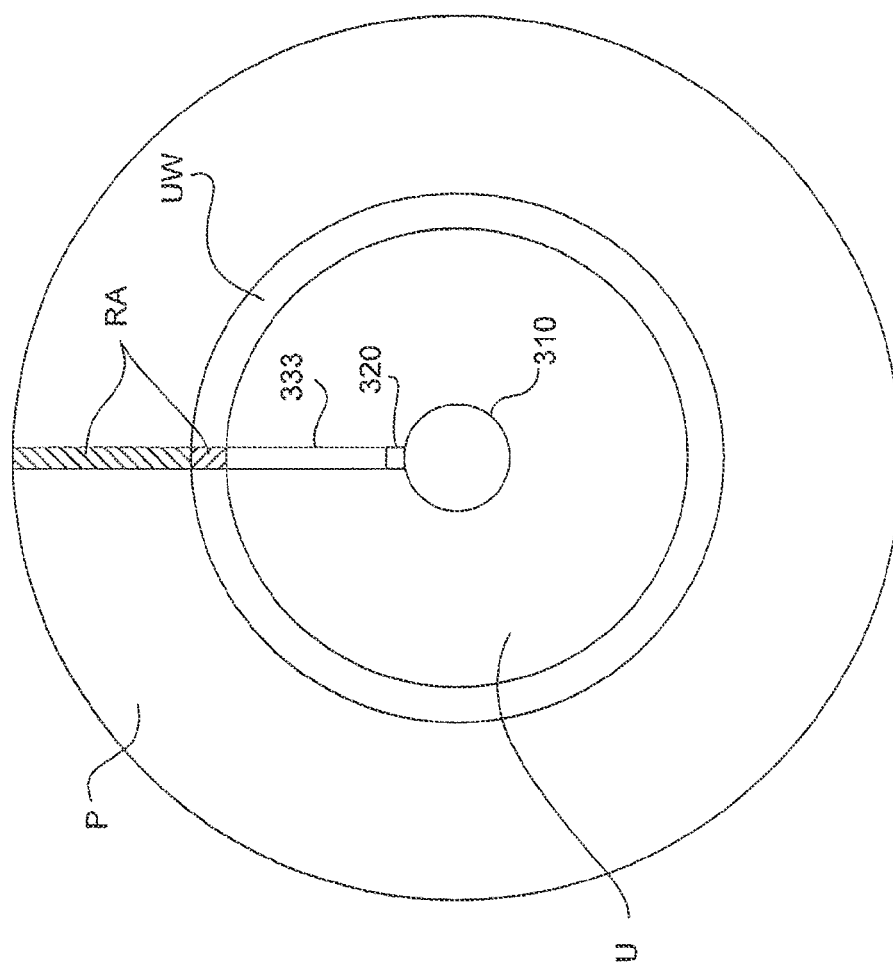
FIG. 10b illustrates a cross-sectional view of a tissue modification device configured to emit a columnar fluid stream.

FIG. 10b shows a cross-sectional view of the device emitting a columnar fluid stream to modify a tissue such as the prostate. An elongate element 310 (such as a shaft, as described above) of the device is disposed within the urethra U. A fluid delivery element 320 disposed on the carrier tube (not shown) within the elongate element 310 is configured to emit a columnar fluid stream 333. As understood herein, the fluid delivery element 320 may comprise a nozzle, as described above, or any other element configured to emit fluid. The columnar fluid stream 333 is configured to resect tissue, such as the urethral wall UW and the prostate tissue P, within a resection area RA.

One characteristic of the columnar fluid stream configuration is that the resection area RA remains substantially constant for some distance from the fluid delivery element 320, since the width of the resection area RA is substantially independent of the fluid distance from the fluid delivery element 320. This is advantageous because the resection area RA remains focused and constant as the fluid stream 333 travels away from the fluid delivery element 320, thereby transmitting energy to the tissue at a focal area. The concentration of energy within a focused resection area RA is particularly advantageous when resecting or penetrating tough tissue, such as the urethral wall UW. In one embodiment, the columnarity of the fluid stream may be varied by introducing pressure fluctuations in the fluid delivery. For example, the columnarity of the fluid stream may be varied by mechanically and controllably introducing a generally solid object in the fluid delivery path, such as behind an aperture of the fluid delivery element 320 or in the path of the fluid stream after it exits an aperture of the fluid delivery element 320. In another example, the columnarity of the fluid stream may be varied by introducing a vibrating element in the fluid pathway, such as a piezoelectric element or the like, to create pressure fluctuations.

In another embodiment, the fluid stream is configured as a diverging fluid stream 334, as seen in FIG. 10*a*. A diverging fluid stream 334 is one in which the fluid exits a fluid stream source, such as the fluid delivery element 320, and diverges substantially in a cone, wherein the tip of the cone is at the fluid stream source. The rate of resection of a diverging fluid stream 334 can be represented as a function of the distance z from the fluid emitting fluid delivery element 320 to the tissue that is to be resected. As shown in FIG. 10*a*, $z_2$ is further away from the orifice than $z_1$, and accordingly the rate of resection at $z_1$ is higher than the rate of resection at $z_2$.

The diverging fluid stream 334 may be characterized by the angle of divergence of the fluid stream. In one embodiment, the angle of divergence is configured to be about 0-90 degrees, more preferably about 2-45 degrees, more preferably about 4-20 degrees, and most preferably about 7 degrees, while it is also contemplated that the angle of divergence may be varied as needed.

Additionally, the diverging fluid stream 334 may be characterized by the cross-sectional shape of the fluid stream. Generally, the diverging fluid stream 334 has a cross-sectional area, or spot-size, that increases at distances further from the fluid stream source (e.g., fluid delivery element 320), thereby proportionally reducing the force of the fluid stream per unit area. This increase of spot-size generally results in greater resection rates of tissue closer to the fluid stream source.

In one embodiment, the cross-sectional shape of the diverging fluid stream 334 is configured as a generally narrow rectangle (for a fan-shaped fluid stream). In another embodiment, the cross-sectional shape of the diverging fluid stream 334 is configured as generally a circle (for a conical-shaped fluid stream), wherein the smallest cross-sectional area is at the fluid stream source. It is noted that the cross-sectional shape of the diverging fluid stream 334 may be configured as any shape that encloses a non-zero area (e.g., an ellipse, or an irregular shape).

Figure 10C:
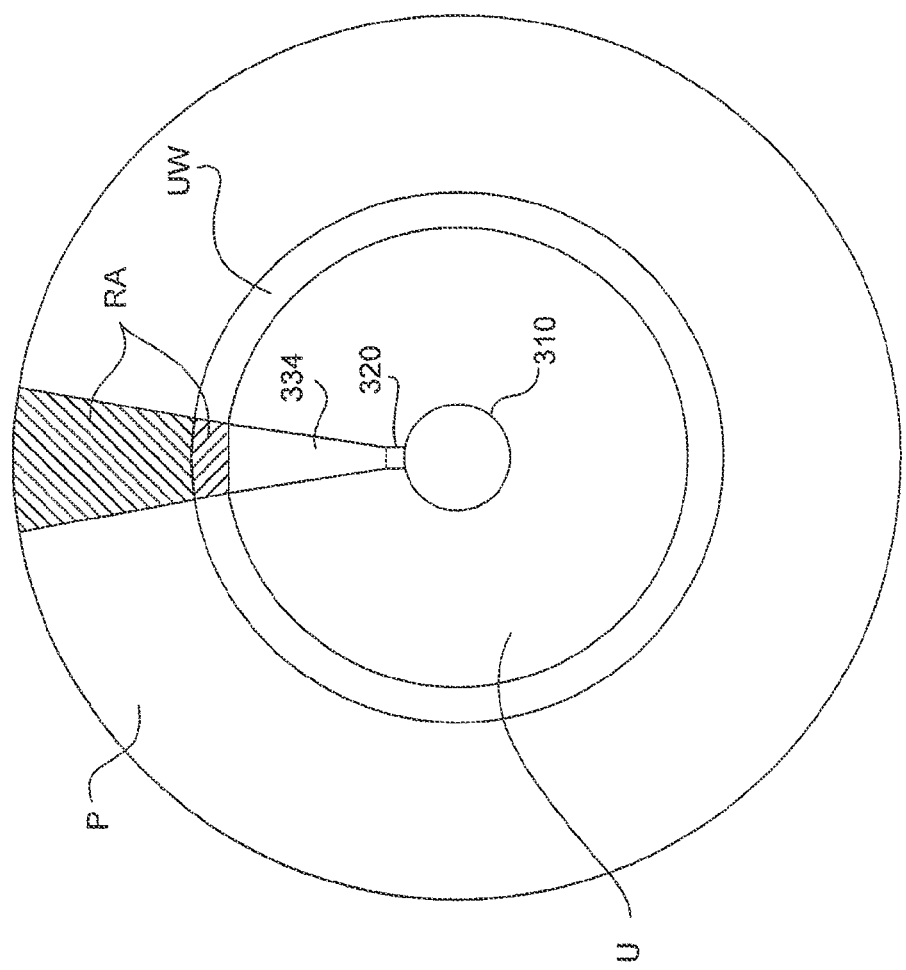
FIG. 10c illustrates a cross-sectional view of a tissue modification device configured to emit a diverging fluid stream.

FIG. 10*c* shows a cross-sectional view of the device emitting a diverging fluid stream to modify tissue such as the prostate. An elongate element 310 of the device is disposed within the urethra U. A fluid delivery element 320 disposed on the carrier tube (not shown) within the elongate element 310 is configured to emit a diverging fluid stream 334. The diverging fluid stream 334 is configured to resect tissue such as the urethral wall UW and the prostate tissue P within a resection area RA. The resection area RA covered by the diverging fluid stream 334 increases as the fluid stream travels away from the fluid delivery element 320, thereby proportionally reducing the strength of the fluid stream per unit area.

A characteristic of the diverging fluid stream 334 is that the resection width increases as a function of distance from the fluid delivery element 320, while the rate of resection per unit area decreases as a function of distance from the fluid delivery element 320. This is because the total energy delivered in the fluid stream is generally constant (not taking into account any decrease in fluid speed), yet the energy is delivered over a larger area. Thus, the energy delivered per area decreases, which is a key parameter upon which the rate of resection depends. Therefore, the rate of resection per unit area decreases as a function of distance.

Furthermore, in a diverging fluid stream 334 the volumetric rate of resection may be substantially constant as a function of distance. That is, while the rate of resection per unit area decreases, the total area resected increases proportionately, and hence the total resected volume remains substantially constant. It is noted that if the areal rate of resection as a function of areal energy density is non-linear and monotonically increasing with energy, then the volumetric rate of resection will decrease as function of distance from the fluid delivery element 320. It is further noted that any slowing of the fluid stream particles (for example, liquid droplets) will also decrease the volumetric resection rate as a function of distance.

The following examples illustrate tissue resection using diverging fluid streams. It is noted that the following configurations are provided as examples and should not be construed as limiting.

EXAMPLE 2: Prostate Penetration Using a Diverging Fluid Stream

Figure 11:
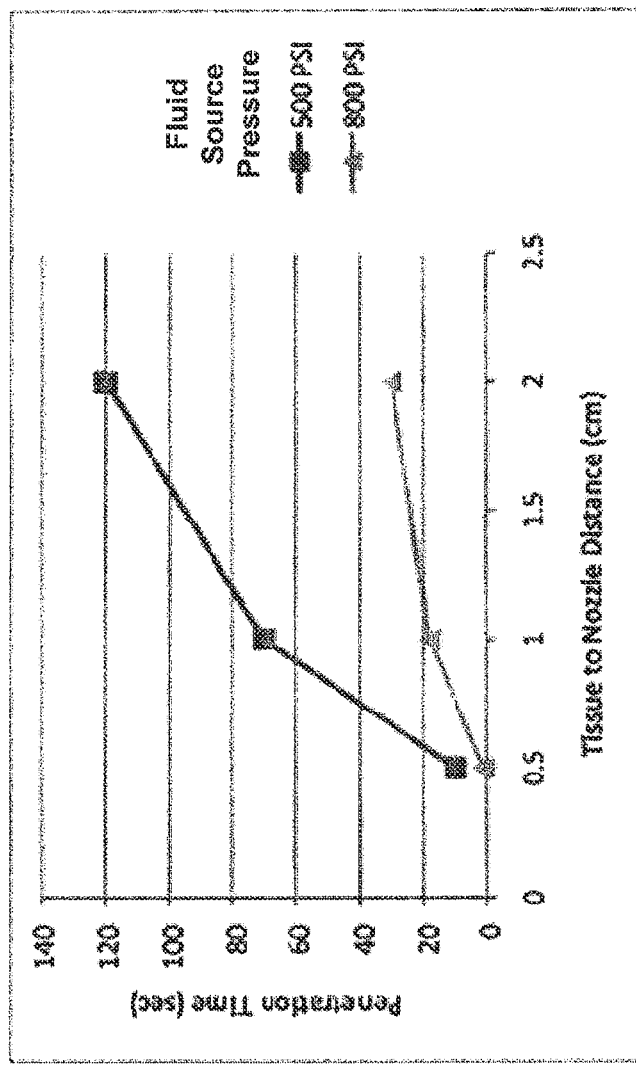
FIG. 11 is a graph of penetration times using diverging fluid streams as a function of the distance between the tissue and the fluid delivery element.

Measured data for resecting tissue of a canine prostate capsule are shown in FIG. 11. The penetration time through the capsule is measured as a function of tissue distance to the fluid delivery element. The angle of divergence of the fluid stream was approximately 7 degrees. The penetration time is plotted as the time to penetrate the capsule, with the capsule having a thickness of less than 1 mm.

FIG. 11 shows an increase in penetration time as the tissue distance to the fluid delivery element increases. It is noted that this effect is stronger at lower fluid source pressures. It is also noted that the penetration time of the columnar fluid stream is generally independent of tissue distance to the fluid delivery element.

Figure 12:
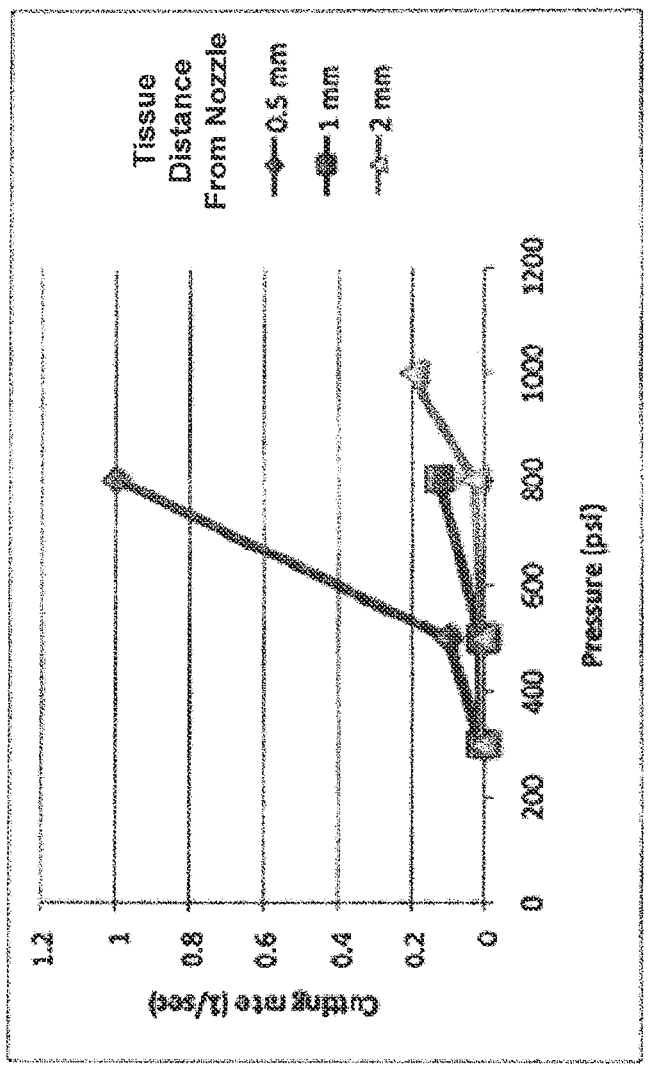
FIG. 12 is a graph of critical pressures as demonstrated by changes in the rates of resection, using diverging fluid streams, as a function of pressure and distance of tissue from the fluid delivery element.

EXAMPLE 3: Critical Pressures and Prostate Tissue Resection Using a Diverging Fluid Stream The variation of critical pressure in diverging-fluid-stream resection as a function of different distances is shown in FIG. 12, as measured on canine prostate capsule tissue. The rate of resection was measured as the inverse of the time taken to resect (i.e., to penetrate) the entire thickness of the capsule. The rate of resection was measured as a function of fluid source pressure and tissue distance from the fluid delivery element. The rate of resection increases at higher pressures for greater distances from the fluid delivery element. This increase in rate of resection is indicative of the critical pressure. The increase in critical pressure as a function of distance shows that in a diverging fluid stream the resection effectiveness decreases with distance.

Figure 13:
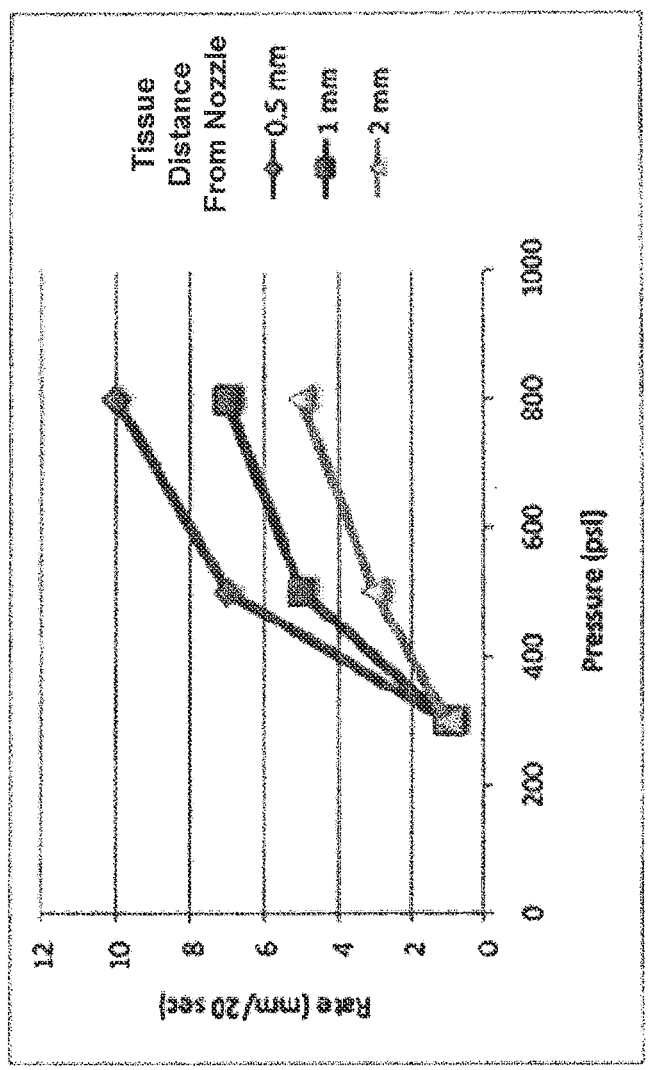
FIG. 13 is a graph glandular tissue resection rates as a function of pressure and distance of tissue from the fluid delivery element.

FIG. 13 illustrates the rate of resection of canine glandular tissue by a diverging fluid stream as a function of source pressure and tissue distance from the fluid delivery element. Above the critical pressure (at approximately 300 psi), the sensitivity to pressure changes is greater when the target tissue is closer to the fluid delivery element. This further aids resection when it is desired to selectively resect glandular tissue while sparing capsular tissue, since a higher pressure may be used to resect the glandular tissue near the fluid delivery element while sparing capsular tissue at a further distance from the fluid delivery element.

Figure 14:
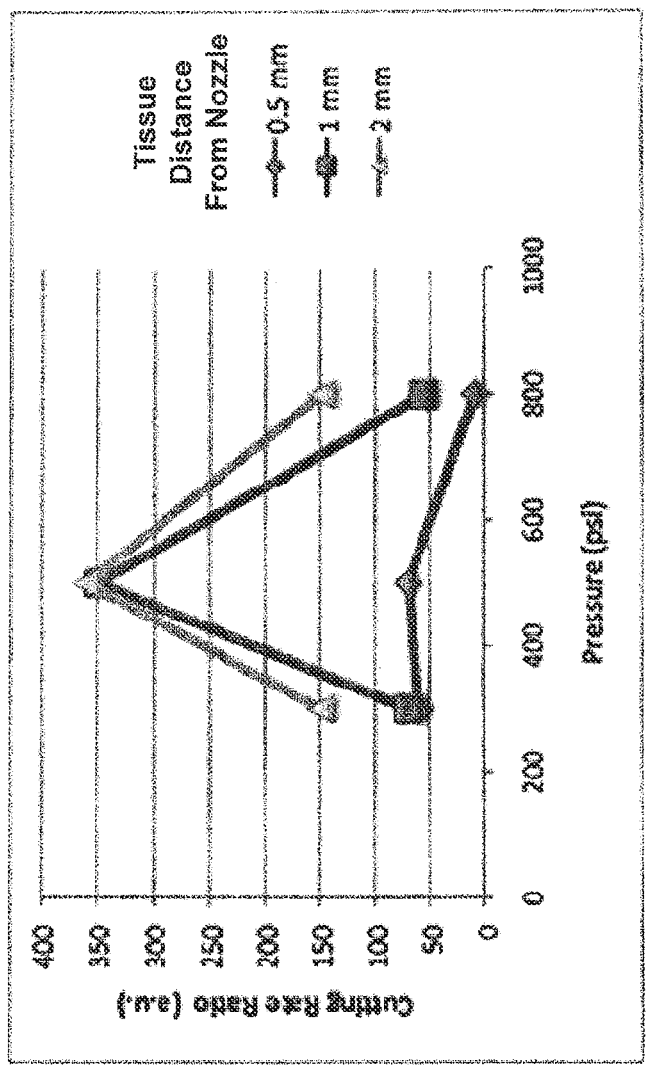
FIG. 14 is a graph of resection rate ratios of glandular tissue to capsular tissue.

The relative rates of resection of two different tissues are shown in FIG. 14 as the ratio of the rate of glandular tissue resection to capsular tissue resection. As seen in FIG. 14, there is a clear maximum ratio at an intermediate pressure, at approximately 500 psi. This is indicative of operating between two critical pressures as described above, and shows that selective tissue resection can be achieved by proper pressure range configuration.

EXAMPLE 4: Critical Distance for Resection Using a Diverging Fluid Stream

For a given pressure, there also exists a critical resection distance when performing diverging-fluid-stream resection, as shown in the table below. As seen in Table 2, penetration of a canine bladder by a diverging fluid stream does not occur when the fluid stream is more than about 10 mm from the tissue, further illustrating the advantage of using a diverging fluid stream for the purpose of selective resection.

TABLE 2

Canine Bladder Resection Using a Diverging Fluid Stream
Canine Bladder Resection
All measurements taken at 1,000 Psi

| Fluid Stream Distance (mm) | Resection Area (mm) | Cut through? |
|---|---|---|
| 25 | 4 | NO |
| 20 | 3.5 | NO |
| 15 | 2 | NO |
| 10 | 1 | YES |
| 3 | 0.5 | YES |

It is an advantageous aspect of the present invention that it allows resection of tissue, such as prostate tissue, without the need to ablate, weaken, mechanically alter, or otherwise treat the tissue prior to resection. While treatments such as tissue ablation could be used to weaken the target tissue by essentially detaching it from the tissue matrix of a body region and thereby allowing easy removal of the pre-treated tissue using a lower strength fluid stream, such treatments require a two-step process (weakening of the tissue followed by detachment of weakened tissue from tissue matrix) and may cause undesirable adverse side-effects such as increased inflammation. Therefore, it is an advantageous aspect that the present invention allows resection of target tissue using a fluid stream and without the need for prior ablation, modification, or treatment of the tissue.

Figure 15:
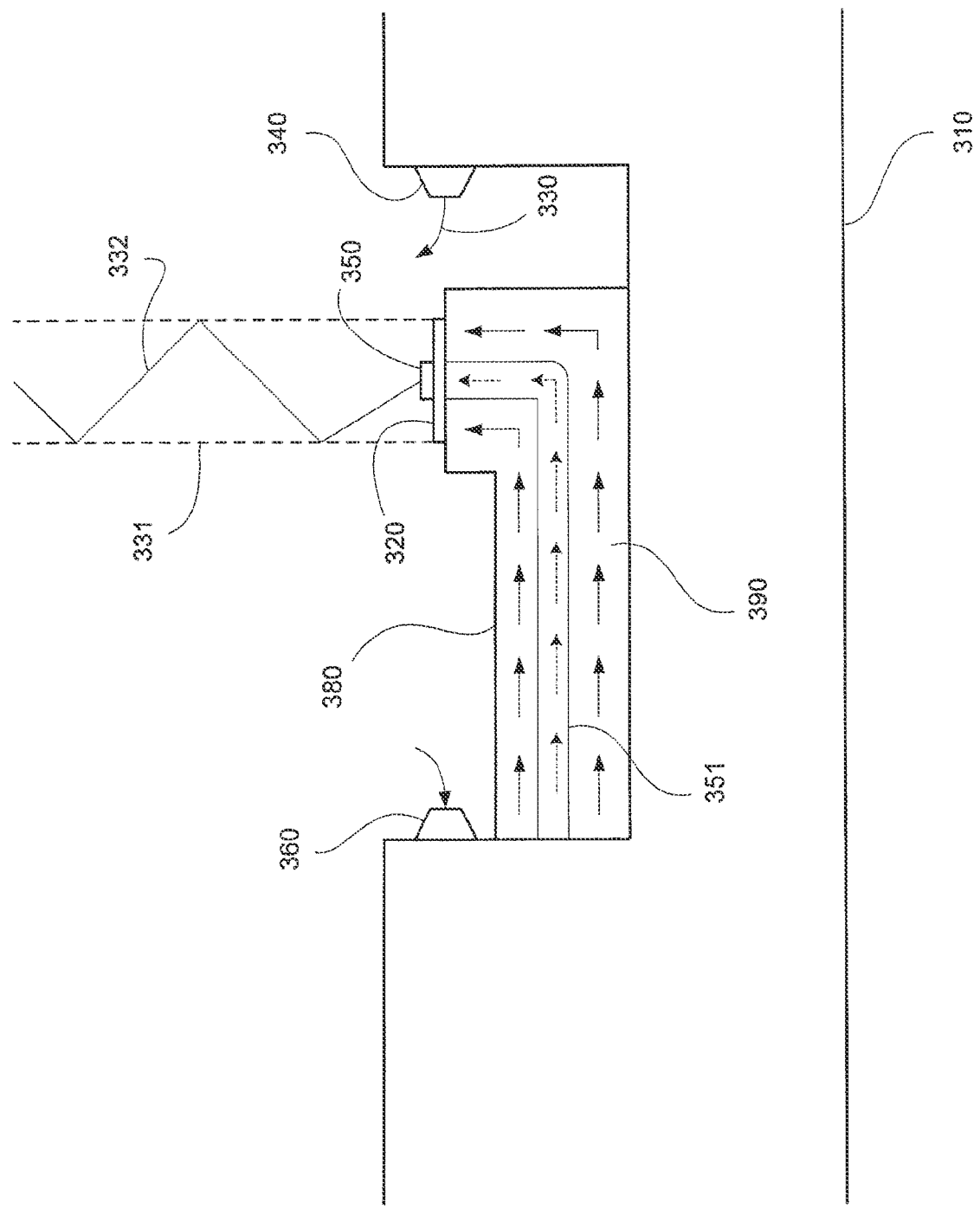
FIG. 15 illustrates a tissue modification device that uses a fluid stream for tissue resection, wherein the fluid stream may optionally act as a conduit for electromagnetic energy.

As described above, the urethral lumen may be insufflated using a fluid in order to create a working space prior to, or while, directing energy to the prostate tissue. FIG. 15 shows an exemplary tissue modification device configured to insufflate and resect tissue. One challenge inherent in tissue modification within a closed tissue system is the lack of adequate working space between the tissue modification device and surrounding tissue of the body region. The presence of such working space would be advantageous, since it would enable increased energy transmission efficiency, efficient means for debris product removal, and better visualization of the tissue region, among other advantages. Devices and methods for tissue modification by creating and utilizing a working space, as well as advantages of such devices and methods, are described in greater detail below. Although the following embodiments are exemplarily described within the context of prostate treatment, it is contemplated that the present invention may be used to modify any tissue within an enclosed tissue system in which one tissue or anatomical structure substantially impinges upon or compresses another tissue or anatomical structure, and in which creating a working space prior to tissue modification is advantageous.

Referring now to FIG. 15, the device comprises an elongate element 310, such as a shaft, configured to be inserted into a body region. The elongate element 310 comprises a window exposing a carrier tube 380 and other components described below. The window reveals a carrier tube 380 and a high pressure fluid delivery element 320 disposed on the carrier tube 380. The fluid delivery element 320 is connected to a fluid source (not shown) via a fluid lumen 390 which delivers fluid from the source to the fluid delivery element 320.

Optionally, when the elongate element 310 is introduced through the urethra, the elongate element 310 may be covered by a sheath or other cover (not shown). When fully covered with the sheath, the window is protected so that it reduces scraping and injury to the urethra as the elongate element 310 is advanced. Once in place, the sheath is retracted, exposing the window. The carrier tube 380 may then be rotated and advanced and/or retracted so that the fluid is delivered through the fluid delivery element 320.

Additionally and optionally, the device may comprise a shield element (not shown) that is positioned to substantially cover the fluid delivery element 320 while maintaining a space between the fluid delivery element 320 and the shield element. This in return effectively maintains that space between the fluid delivery element 320 and any tissue that might impinge on the shield element. In one embodiment, the shield element is a substantially flat sheet-like element positioned over the fluid delivery element 320. The shield element is positioned or shaped such that it allows the carrier tube 380 to move within the elongate element 310 as needed. For example, the shield element may be curved to follow a curvature of the carrier tube 380. The shield element comprises an opening to allow the fluid stream emitted by the fluid 10 delivery element 320 to travel unobstructed through the opening and impinge on the tissue. The opening may be circular, or it may comprise other shapes. One advantage of such a shield element is that it protects the fluid delivery element 320 from being damaged during insertion or removal procedures and/or during treatment. Another advantage of the shield element is that, during or after fluid emission, fluids that are returning back towards the fluid delivery element 320 may travel through the shield element opening (or through other paths around the shield element) and into the space between the shield element and the fluid delivery element 320. Such returned fluids may then be channeled out of that space such that fluid emission is not obstructed or hindered by such returned fluids.

The shield element may further be configured such that the space between the shield element and the fluid delivery element 320 is in continuous communication with a waste disposal lumen via a low-flow-resistance fluid path. This creates a low-flow-resistance path between the fluid delivery element 320 and an external destination of such waste, such that waste and fluids leaving the fluid delivery element 320 may easily leave the region surrounding the fluid delivery element 320. Low resistance in this case is understood to mean a flow resistance that is lower in comparison with a flow resistance of the fluid delivery element 320. This configuration advantageously prevents back-pressure at the fluid delivery element 320, which would otherwise reduce flow, and thereby allows the fluid stream emitted by the fluid delivery element 320 to travel substantially undisturbed by waste and return fluids.

The fluid delivery element 320 may be a single nozzle, a plurality of nozzles, or an array of nozzles of various configurations. The fluid delivery element 320 is configured to emit a fluid radially outwardly as a fluid stream 331, with sufficient force so that upon contact with the tissue the fluid stream 331 resects the tissue. The fluid stream 331 may be perpendicular to the elongate element 310, or it may be configured to be at various angles relative to the elongate element 310.

The carrier tube 380 may be axially translated, rotated, oscillated, or rotationally oscillated relative to the elongate element 310 so that the fluid stream 331 can be scanned or rastered to resect a desired area or volume of the tissue. The desired area or volume may be spherical, cylindrical, or any other predetermined area or volume of arbitrary shape and dimension.

Additionally and optionally, when the device is not being used to resect tissue, the carrier tube 380 may be positioned so that the fluid delivery element 320 and/or any other elements (such as visualization or cauterization elements) are positioned away from the window, thereby reducing the risk of damage to such elements, as well as reducing any risk of unintentional resection of the tissue.

The device further comprises at least one insufflation port 340 disposed on the elongate element 310. The insufflation port 340 is connected via one or more lumens to an insufflation source (not shown), wherein the insufflation source delivers a fluid 330 into the body region through the insufflation port 340 in order to expand the surrounding tissue and create a working space. The device further comprises at least one removal port 360 for the removal of debris products, such as resection products, resection fluid, other waste products, or a mixture thereof. The elongate element 310 may include lumens, passages, electrically conductive wires, and the like, configured to deliver energy and/or materials from the proximal end to the distal end of the elongate element 310 and/or to remove debris and waste products, details of which are described above.

Optionally, in addition to the fluid delivery element 320, the device may comprise an electromagnetic energy delivery port 350 disposed on the carrier tube 380 and positioned near or within the fluid delivery element 320. Electromagnetic energy 332 is delivered to the energy delivery port 350 by means of one or more conduits 351, such as optical fibers or other waveguides within the carrier tube 380 and the elongate element 310, as also described in greater detail above. The electromagnetic energy 332 may be radiofrequency energy, coherent or non-coherent light, or any other modality of electromagnetic energy. The energy delivery port 350 is configured to deliver the energy 332 through the interior of the fluid stream 331 so that the electromagnetic energy 332 may resect the tissue in lieu of, or in combination with, the fluid resection.

Additionally and optionally, the various electromagnetic energy modalities described above may be configured to cauterize the tissue, in combination with tissue resection, or independently thereof. Since selective tissue resection as disclosed herein generally causes little or no damage to remaining tissue such as vascular tissue and therefore causes limited or no bleeding, such cauterization need only be used on a limited basis, if at all. It is contemplated that when electromagnetic energy is delivered to the tissue by the fluid stream 331 for cauterization, the fluid source pressure may be adjusted to be generally below the critical pressure for tissue resection such that no additional tissue is resected. Alternatively or additionally, cauterization may be achieved using other means, for example using a cauterizing balloon and/or stent placed in contact with tissue using a catheter device, as described above.

Furthermore, the device may comprise optional deflective elements, for example positioned within the interior or the elongate element 310 and away from the window, configured to deflect fluid, emitted by the fluid delivery element 320, back towards the fluid delivery element 320, thereby removing any debris that may have accumulated on the fluid delivery element 320 and/or energy delivery port 350 during tissue resection. Furthermore, the fluid delivery element 320 in combination with the deflective elements may be configured to clean a part of, or substantially the entirety of, the fluid delivery element 320, any visualization or cauterization elements, and/or carrier tube 380. The deflective element may be configured to be substantially flat or concave. Alternatively the deflective element may be configured as any shape or design.

Additionally, the deflective element may act be configured as a protective element for the fluid delivery element. The fluid delivery element may be positioned at a specific location relative to the protective element that protects the prostate from unexpected fluid emissions and protects the fluid delivery element 320 from, for example, clogging or obstruction by tissue, especially during insertion and removal from the body.

Figure 16:
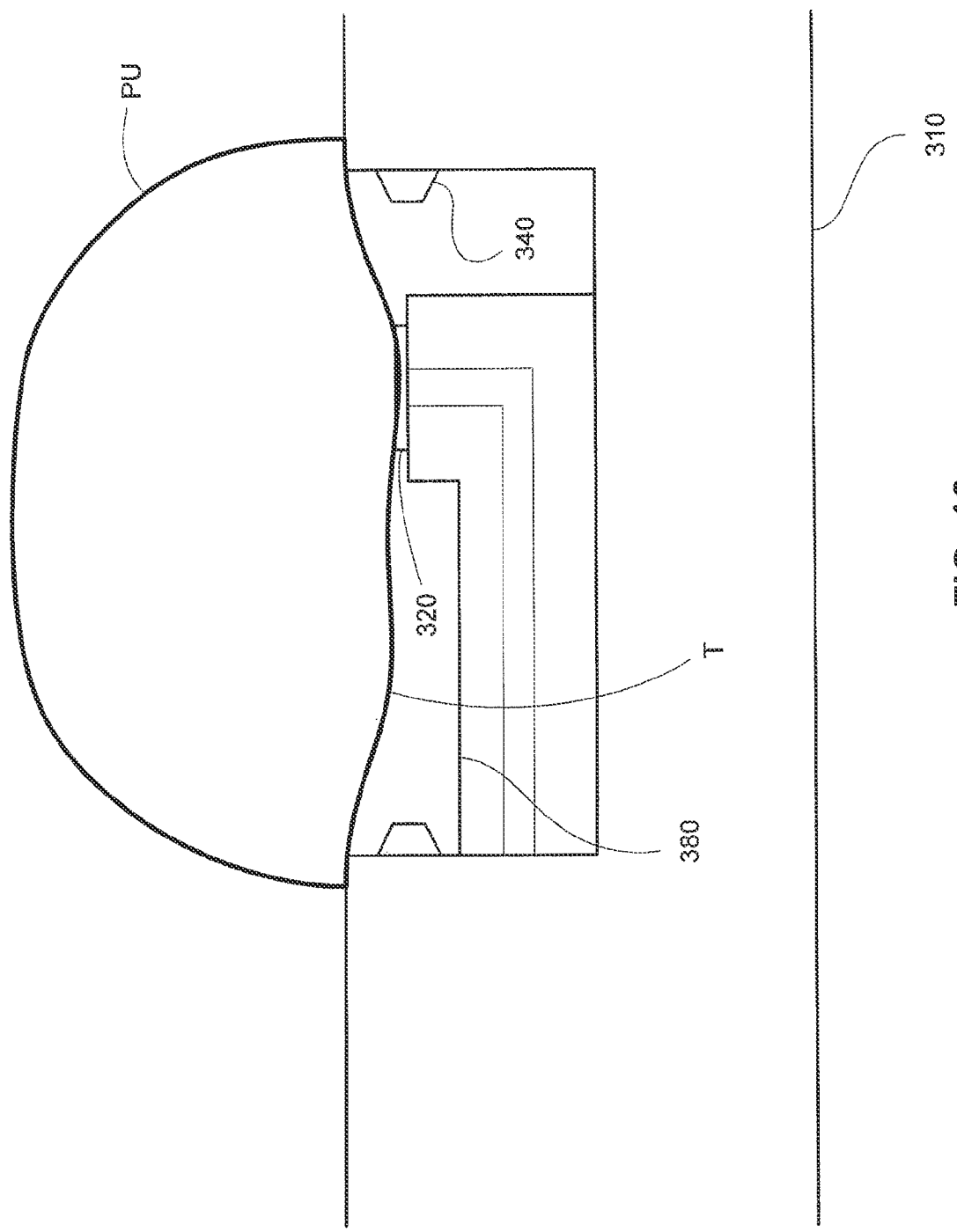
FIG. 16 illustrates a tissue modification device positioned in the urethra, wherein tissue contact with the device causes inefficient device operation.
Figure 17:
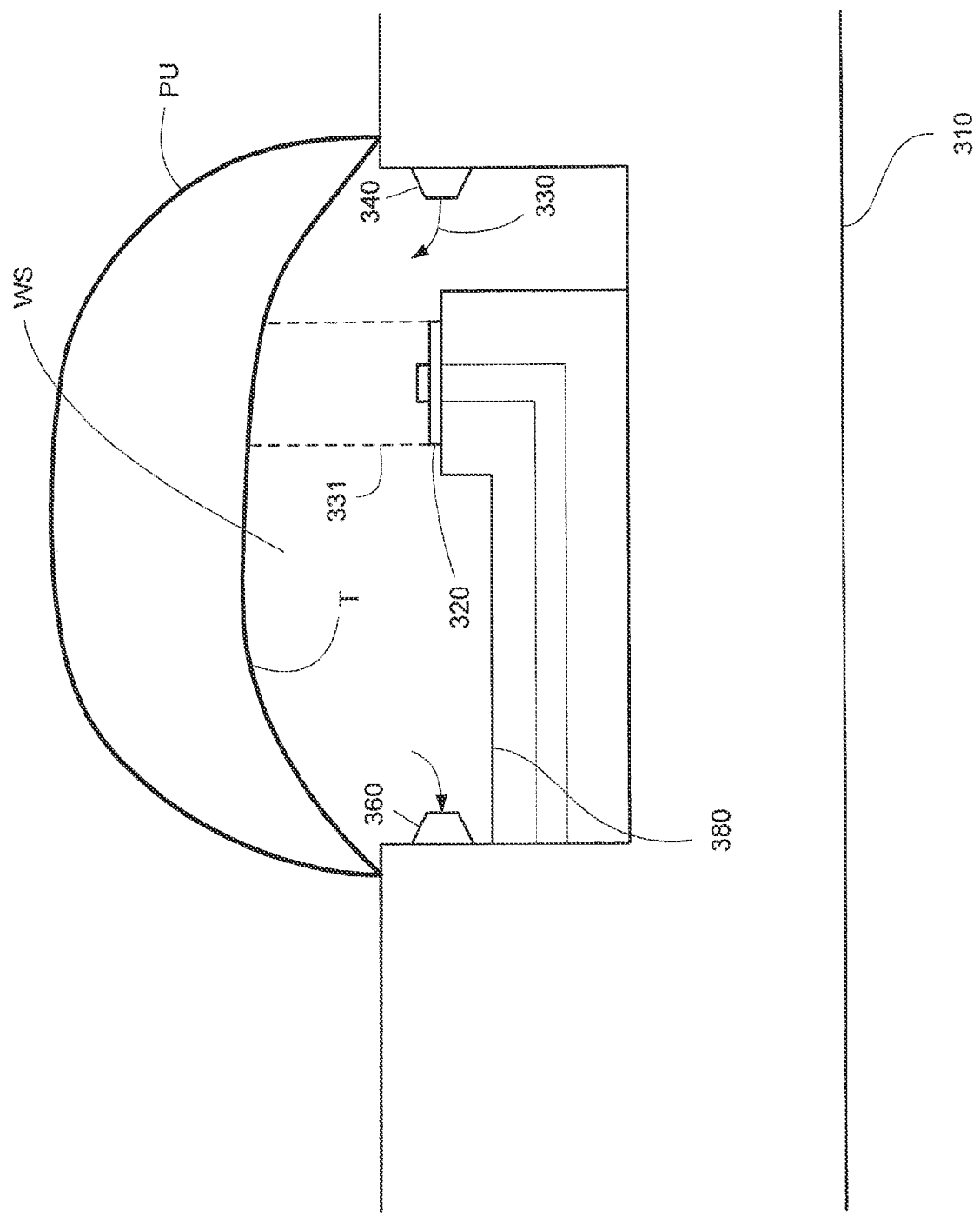
FIG. 17 illustrates a tissue modification device positioned in the urethra as seen in FIG. 16, with the device expanding the surrounding tissue and creating a working space.

Referring now to FIG. 16, the tissue modification device is shown introduced into a body region. The body region is exemplarily shown as the prostate-urethra region PU. Due to abnormalities such as BPH or other tissue characteristics, the device may be obstructed by surrounding tissue T, which complicates treatment. As shown in FIG. 16, after the elongate element 310 has been introduced into the urethra, the surrounding tissue T may effectively block the fluid delivery element 320 and prevent the carrier tube 380 from properly axially translating, rotating, oscillating, or rotationally oscillating relative to the elongate element 310. To resolve this shortcoming, as seen in FIG. 17, the device is configured to expand the surrounding tissue T, thereby creating a working space WS within which the device may resect the tissue T using fluid stream 331.

Expansion of the surrounding tissue T may be accomplished in a variety of ways. In one embodiment, the device is configured to expand the surrounding tissue T by delivering a first fluid 330 via the insufflation port 340. The fluid 330 contacts and thus expands the surrounding tissue T, thereby creating a working space WS around the carrier tube 380 and the fluid delivery element 320.

In another embodiment, the device is configured to expand the surrounding tissue T by mechanical means. In one such embodiment, one or more stents or mechanical structures may be disposed on the elongate element 310 and expanded within the body region. Expansion may be accomplished by using one or more inflation balloons, or by configuring the stent to exhibit a shape memory effect (such as a Nitinol stent) that causes the stent to expand upon release from a confined space. Alternatively, the stent may be expanded by other means, as should be known to those of ordinary skill in the art. In another embodiment, one or more expansion balloons disposed on the elongate element 310 are used to expand the surrounding tissue T. The balloons may be inflated by a fluid such as a gas or liquid.

It is contemplated that creating a working space WS in a body region may comprise expanding the surrounding tissue T, stretching the surrounding tissue T, repositioning the surrounding tissue T, unfolding the surrounding tissue T, and/or any other ways of creating a working space WS within a body region.

Once a working space WS has been created, the carrier tube 380 may axially translate, rotate, oscillate, or rotationally oscillate relative to the elongate element 310 and unhindered within the working space WS, with the fluid delivery element 320 no longer blocked by surrounding tissue T. At this point, the device may effectively start the treatment by delivering a second fluid 331, as a fluid stream, to resect the surrounding tissue T.

There are a number of advantages in having fluids 330 and 331 be of different mediums, as will be described further below. In one exemplary embodiment, the first fluid 330 used to expand the tissue and create the working space WS is a gas, such as pressurized $CO_2$, CO, $N_2$, He, Ar, other biologically compatible gas, or a combination thereof. The second fluid 331 used to resect tissue is a liquid such as water, saline, other biologically compatible liquid, or a combination thereof Additionally and optionally, the second fluid 331 may comprise one or more soluble substances such as sodium chloride or barium sulphate. One advantage of using such soluble substances is that it increases the efficiency of resection by adding corrosive strength to the second fluid 301. Indeed, depending on the concentration of the soluble substances present in the second fluid 301, the increase in efficiency of resection may lead to a decrease of the fluid pressure necessary for resection. Another advantage of using such soluble substances is that they may aid in preventing or reducing bleeding.

Alternatively and optionally, it is contemplated that the second fluid 331 may further comprise generally crystalline particles that may increase the efficiency of resection and lead to a decrease of the fluid pressure necessary for resection. In one embodiment, the crystalline particles may be calcium, magnesium, aluminum, manganese, iron, nickel, copper, zinc, strontium, barium, bismuth, chromium, vanadium, lanthanum, their salts, or a combination thereof. In another embodiment, the crystalline particles may be cation salts such as formate, fumarate, acetate, propionate, butyrate, caprylate, valerate, lactate, citrate, malate, gluconate, chloride, potassium, phosphate, or a combination thereof. In yet another embodiment, the crystalline particles may be calcium citrate, calcium tartrate, calcium succinate, calcium fumarate, calcium adipate, calcium malate, calcium lactate, calcium gluconate, dicalcium phosphate dehydrate, calcium diphosphate, dicalcium phosphate anhydrous, calcium chloride, calcium acetate monohydrate, or a combination thereof. Furthermore, it is envisioned that the crystalline particles may be any solid particles.

The crystalline particles may have a lifetime of at least 30 days, at least 10 days, at least 1 day, at least 1 minute, at least 10 seconds, or at least 1 second. Furthermore, it is envisioned that the dimension of the crystalline particles may be smaller than the dimension of an aperture of the fluid delivery element 320 such that the particles are sufficiently small to pass through the fluid delivery element 320. Further, the particles are configured to be sufficiently small such that the fluid delivery element 320 is not obstructed or clogged. To achieve this, the largest dimension of the particles may generally be a fraction of the smallest dimension of the fluid delivery element opening or openings, wherein the fraction is preferably in the range of about 1/10 to 1/2. In one embodiment, the largest dimension of the crystalline particles is generally smaller than 1/2 of the smallest dimension of the aperture of the fluid delivery element 320. In another embodiment, the largest dimension of the crystalline particles is generally smaller than 1/4 of the smallest dimension of the aperture of the fluid delivery element 320. In yet another embodiment, the largest dimension of the crystalline particles is generally smaller than 1/10 of the smallest dimension of the aperture of the fluid delivery element 320.

Additionally, the second fluid 331 may comprise one or more dissolved gases to increase the efficiency of resection. Such dissolved gases may include $CO_2$, CO, $N_2$, He, Ar, other biologically compatible gases, or a combination thereof. In one embodiment, the device is configured such that gas bubbles form after emission of the second fluid 331 from the fluid delivery element 320 but before the fluid 331 reaches the tissue. In another embodiment, the device is configured such that gas bubbles form in the second fluid 331 upon impact with tissue. The device may be configured to use a combination of such effects, with some of the gas bubbles forming before impact with tissue and some forming upon impact.

Optionally, the temperature of the second fluid 331 may be configured to be significantly lower than the tissue temperature to cause vascular constriction and thereby reduce or inhibit bleeding. Additionally, the temperature of the second fluid 331 may be configured to have an elevated temperature, for example of sufficient elevation to aide in resection or cauterization.

It is contemplated that the pressure of the first fluid 330 configured as a gas is within the range of about 0.1-5.0 psi, preferably within the range of about 0.5-2.5 psi. Optionally, a pressure sensor may be provided to monitor the pressure of the first fluid 330, such that the pressure may be maintained within a desired range. It is further contemplated that the source pressure of the second fluid configured as a liquid is within the range of about 1-2,000 psi, more preferably within the range of about 50-1,500 psi, and most preferably within the range of about 100-1,000 psi.

Optionally, the insufflation port 340 may be disposed on the elongate element 310 in close proximity to the fluid delivery element 320. In such a configuration, some of the first fluid (e.g., gas) 330 delivered by the insufflation port 340 into the working space WS is carried outwardly by the fluid stream comprising the second fluid (e.g., liquid) 331 to form an envelope around the resecting fluid stream, thereby helping to preserve stream integrity. The proximity of the insufflation port 340 to the fluid delivery element 320 may also protect the fluid delivery element 320 from accumulation of fluids and tissue, thereby maintaining the integrity of the fluid stream.

Figure 18:
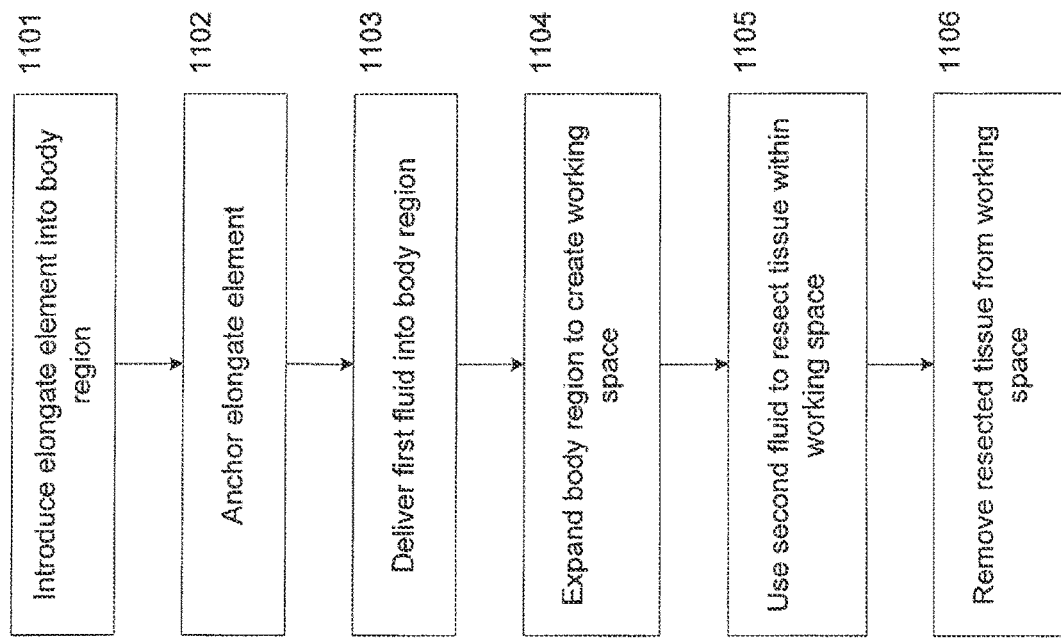
FIG. 18 is a flow diagram illustrating an operation of the tissue modification device.

FIG. 18 is a flow diagram illustrating an exemplary operation of the device. At step 1101, the elongate element 310 is introduced into a body region such as the prostate-urethra region PU. At step 1102, the elongate element 310 is maneuvered into a position and an anchoring element (not shown) is engaged to stabilize the elongate element 310 for the remainder of the operation. The anchoring element may comprise an anchoring balloon and/or an external anchoring frame, wherein the anchoring balloon and the external anchoring frame are configured to substantially prevent proximal and distal dislodgement of the elongate element 310 by stabilizing the elongate element 310 within the treatment region.

The anchoring balloon is configured to inflate just distal of the bladder neck. The anchoring balloon may be inflated to occupy a sufficient portion of the bladder to prevent the elongate element 310 from moving substantially beyond the treatment region (in a direction away from the bladder) during the operation. Inflation of the anchoring balloon may be accomplished by various means described above. Alternatively, other expansion structures, such as a Nitinol semi-arch scaffold, may be used as an anchoring element instead of a balloon.

The external anchor frame is configured to engage an external body surface area, for example, the surface area at the base of the penis. The external anchor frame typically comprises an atraumatic ring for engaging the external body surface area. In one embodiment, once the elongate element 310 has been introduced into the treatment region and the anchoring balloon is expanded to occupy a portion of the bladder, the external anchor frame then coaxially advances automatically or manually over the penis such that the atraumatic ring engages the external body surface area at the base of the penis. Once the external anchoring frame engages the external body surface area, the elongate element 310 is prevented from moving substantially beyond the treatment region (in a direction towards the bladder). The anchoring element, comprising the anchoring balloon and the external anchoring frame, is configured to substantially stabilize the elongate element 310 by preventing proximal and distal dislodgement beyond the treatment region since the elongate element 310 is substantially compressed within the treatment region. The device stability provided by the anchor element also allows precision movement of the fluid delivery element which in turn aids in automation of the treatment procedure. Advantageously, it is noted that in such an embodiment configured to use an external anchoring frame in combination with a balloon, the balloon need not substantially fill the entire bladder to stabilize the device, since inflating the balloon to fill a portion of the bladder can provide sufficient stabilization. The anchoring procedure is also described in co-pending Patent Application Publication No. 2009/0227998.

At step 1103, after the elongate element 310 is stabilized at its location, the window cover on the elongate element 310 may be retracted to reveal the insufflation port 340, the removal port 360, and the carrier tube 380.

At step 1104, the insufflation port 340 delivers the first fluid 330 into the body region and causes the surrounding tissue T to expand, thereby creating a working space WS. At step 1105, the fluid delivery element 320 delivers a second fluid 331 as a fluid stream to resect the 15 surrounding tissue T within the working space WS.

As mentioned above, there are a number of advantages in having the first fluid 330 and second fluid 331 be of different mediums. For example, when expansion fluid 330 is of a lower viscosity medium than the resection fluid 331, the fluid source pressure or flow rate required to resect the tissue using the second fluid 331 is less than when the working space WS is filled with a fluid that is of the same (or higher viscosity) medium as the second fluid 331. This is so because, were the second fluid 331 to travel through a working space WS filled with a first fluid of the same or higher viscosity medium, the second fluid 331 would have to overcome greater resistance in the working space WS before reaching the target tissue.

Another advantage of a two medium embodiment is related to fluid stream integrity. The friction or resistance between the first fluid 330 in the working space WS and the fluid stream comprising the second fluid 331 causes the fluid stream to gradually lose its structural integrity by causing a portion of the second fluid 331 to disperse from the stream. Such dispersion may be undesirable, since a fluid stream that suffers from significant dispersion may arrive at the surrounding tissue T with decreased resection effectiveness and may additionally cause damage to surrounding healthy tissue by decreasing the accuracy of the resection. To maintain fluid stream integrity in such a high-resistance working space WS, increased pressure would have to be applied to liquid 331 in an effort to counteract the rate of fluid dispersion. In contrast, by creating a working space WS comprising a first fluid 330 of lower viscosity medium (e.g., a gas) than that of the fluid stream 331, a lower source pressure or flow rate configuration may be used for the fluid stream 331 while maintaining adequate fluid stream integrity and resection effectiveness. Alternatively, the resistance between the first fluid 330 and the second fluid 331 may be configured to induce dispersion of the fluid stream such that the resection force is reduced at desired distances away from the fluid delivery element 320. The first fluid 330 may be adjusted (e.g., pressure of a gas) to configure the distance at which the dispersion affects the resection rate in a desired manner.

Another advantage of a two medium embodiment is related to the difference in refractive indices of the two mediums. In an optional embodiment, at step 1105, electromagnetic energy 332 may be delivered through the interior of the fluid stream to cauterize the tissue, to resect the tissue, or a combination thereof. In such an embodiment, the resecting fluid stream acts as a conduit for the electromagnetic energy transmission, and the refractive index difference between the fluid in the working space WS and the resecting fluid stream can be configured to allow for more efficient energy conduction within the interior of the resection fluid stream. It is further contemplated that, when acting as the conduit for electromagnetic energy transmission, the fluid stream may be configured to have a flow and force that are sufficient to transmit energy to the tissue but not sufficient to resect the tissue.

In particular, when the refractive index of the first fluid 330 is configured to be less than the refractive index of the second fluid 331 (e.g., gas and liquid, respectively), total or near total internal reflection may be achieved within the fluid stream. In such configuration, more of the electromagnetic energy traveling through the fluid stream reaches the target tissue at the desired location, and less of the electromagnetic energy is likely to diffuse out into the working space WS. Therefore, as a result of the increased conduction efficiency, the amount of the electromagnetic energy 332 at the source can be reduced while maintaining cauterization and/or ablation effectiveness, thereby decreasing the power consumption of the device and reducing any hazardous radiation effects on the patient. Electromagnetic energy types contemplated by the present invention include radio frequency energy and light energy, such as coherent (e.g., laser energy) or non-coherent light.

At step 1106, resection debris products (along with the fluid used for resection) are removed from the working space WS through the removal port 360. In one embodiment, debris products may be removed through the removal port 360 by creating a positive pressure differential between the removal port 360 and the insufflation port 340, such that debris products travel through the removal port 360 and are thereby removed. In another embodiment, removal may be accomplished by attaching a vacuum source to the removal port 360 and applying suction to the working space WS. Optionally, a combination of the two removal methods may be used.

It is contemplated that steps 1103, 1104, 1105, and 1106 described above may be practiced contemporaneously with each other. For example, tissue resection as described in step 1105 may be performed at the same time as debris product removal as described in step 1106.

Optionally, the treatment may be visualized by providing visualization elements within the expanded working space WS. Such visualization elements may comprise endoscopic cameras or other suitable visualization elements. In one embodiment, the visualization elements may be disposed on the elongate element 310 or on the carrier tube 380. In another embodiment, the visualization elements may be separately inserted into the working space WS.

Additionally and optionally, it is contemplated that the first fluid 330 may be continuously delivered into the body region during treatment to maintain the working space WS. Furthermore, when a sufficient working space WS is already present in the body region prior to the delivery of the first fluid 330, the first fluid 330 may be delivered into the body region to maintain such working space WS.

It is further contemplated by the present embodiments, that the second fluid 331 may be combined with a therapeutic agent to treat the surrounding tissue T. The therapeutic agent may be utilized to minimize patient discomfort, bleeding, and/or to provide localized treatment for cancer, prostatitis, or other ailments. It is envisioned that the therapeutic agent may comprise soluble substances such as salts (e.g., those described above), antibiotics, coagulants, anesthetics, vasoconstrictors, anti-inflammatory agents, chemotherapeutic agents, anti-carcinogenics, other additives or drugs, or a combination thereof. Additionally, it is contemplated that the therapeutic agent may be a fixation agent, such as glutaraldehyde, to contract the tissue T in order to minimize bleeding. It is noted that glutaraldehyde may also aid in enlarging the working space WS by causing tissue shrinkage and enlargement of the urethral lumen.

The therapeutic agent may be delivered to the tissue T during tissue resection, prior to tissue resection, after tissue resection, or independent of tissue resection. When the therapeutic agent is delivered to the tissue T during resection, the second fluid 331 with pressure configurations as described above may be used. When the therapeutic agent is delivered to the tissue T prior to and/or after tissue resection or independent of tissue resection to lavage the working space WS, the pressure of the second fluid 331 may be adjusted below the critical pressure required to resect the tissue T. In such as embodiment, the pressure of the second fluid source prior to and/or after tissue resection may be within the range of about 1-50 psi, or alternatively less than about 10 psi. Alternatively and optionally, the therapeutic agent may be delivered to the tissue T using a short pulsed emission of second fluid 331 above the critical pressure that effectively injects the agent into the tissue T with minimal damage to the tissue T. Depending on the desired treatment, the strength of such emission may be configured such that the agent is injected at an appropriate depth into the tissue T.

While the present embodiments have been described primarily with reference to transurethral treatment of the prostate, it is contemplated that certain aspects of the embodiments may also be used to treat and modify other organs such as brain, heart, lungs, intestines, eyes, skin, kidney, liver, pancreas, stomach, uterus, ovaries, testicles, bladder, ear, nose, etc., soft tissues such as bone marrow, adipose tissue, muscle, glandular tissue, spinal tissue, etc., hard biological tissues such as teeth, bone, etc., as well as body lumens and passages such as the sinuses, ureter, colon, esophagus, lung passages, blood vessels, etc. The devices disclosed herein may be inserted through an existing body lumen, or inserted through solid body tissue.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A tissue treatment device comprising:
a shaft having a proximal end and a distal end; and
an energy source positioned in an energy delivery region on the shaft configured to deliver an energy radially outwardly;
wherein the energy source is adapted to be translated and rotated relative to the shaft to selectively direct the energy from the energy source to treat different regions of a tissue and wherein the tissue comprises a prostate tissue and the energy source is adapted to be placed in a urethra of a patient to treat the prostate tissue, wherein the energy source comprises an electrode and the electrode comprises a laterally projecting electrode configured to engage against tissue and deliver radio frequency energy to ablate the tissue;
wherein the shaft has a width in a range from 1 mm to 10 mm and a length in a range from 15 cm to 25 cm.

2. The tissue treatment device of claim 1, further comprising a lumen in the shaft configured for one or more of insufflation, pressurization, aspiration, or flushing.

3. The tissue treatment device of claim 1, further comprising an expandable anchor near the distal end for anchoring in a bladder.

4. The tissue treatment device of claim 3, wherein the expandable anchor comprises a balloon adopted to expand to occupy an interior of the bladder when it is inflated.

5. The tissue treatment device of claim 1, wherein the energy source comprises a laser energy source.

6. The tissue treatment device of claim 5, wherein the energy source further comprises a mirror for reflecting laser energy.

7. The tissue treatment device of claim 1, wherein the energy source comprises a conductive fluid source and a radiofrequency energy source.

8. The tissue treatment device of claim 1, wherein the energy source comprises one or more of a laser energy source, a radiofrequency energy source, a thermal energy source, a mechanical energy source, a vibrational energy source, or a cooling energy source.

9. The tissue treatment device of claim 8, wherein the energy source comprises the thermal energy source.

10. The tissue treatment device of claim 8, wherein the energy source comprises a plurality of energy sources.

11. A tissue treatment device comprising:
a shaft having a proximal end and a distal end; and
an energy source positioned in an energy delivery region on the shaft configured to deliver an energy radially outwardly;
wherein the energy source is adapted to be translated and rotated relative to the shaft to selectively direct the energy from the energy source to treat different regions of a tissue and wherein the tissue comprises a prostate tissue and the energy source is adapted to be placed in a urethra of a patient to treat the prostate tissue and wherein the energy source comprises an electrode and the electrode projects laterally from a tube;
wherein the shaft has a width in a range from 1 mm to 10 mm and a length in a range from 15 cm to 25 cm.

12. A tissue treatment device comprising:
a shaft having a proximal end and a distal end; and
an energy source positioned in an energy delivery region on the shaft configured to deliver an energy radially outwardly;
wherein the energy source is adapted to be translated and rotated relative to the shaft to selectively direct the energy from the energy source to treat different regions of a tissue and wherein the tissue comprises a prostate tissue and the energy source is adapted to be placed in a urethra of a patient to treat the prostate tissue and wherein the energy source comprises an electrode and the electrode is configured to ablate tissue and to cauterize tissue after ablation by changing a radiofrequency energy;

wherein the shaft has a width in a range from 1 mm to 10 mm and a length in a range from 15 cm to 25 cm.

13. A tissue treatment device comprising:

a shaft having a proximal end and a distal end; and an energy source positioned in an energy delivery region on the shaft configured to deliver an energy radially outwardly;

wherein the energy source is adapted to be translated and rotated relative to the shaft to selectively direct the energy from the energy source to treat different regions of a tissue and wherein the tissue comprises a prostate tissue and the energy source is adapted to be placed in a urethra of a patient to treat the prostate tissue and wherein the energy source comprises an electrode and the electrode is configured to deliver electrical energy in either a monopolar or bipolar mode;

wherein the shaft has a width in a range from 1 mm to 10 mm and a length in a range from 15 cm to 25 cm.

* * * * *